(12) United States Patent
Brandeis

(10) Patent No.: US 10,709,540 B2
(45) Date of Patent: Jul. 14, 2020

(54) VESSEL OCCLUSION DEVICES, KITS AND METHODS

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 469 days.

(21) Appl. No.: 15/044,141

(22) Filed: Feb. 16, 2016

(65) Prior Publication Data

US 2016/0157986 A1 Jun. 9, 2016

Related U.S. Application Data

(62) Division of application No. 14/411,388, filed as application No. PCT/IL2013/050537 on Jun. 25, 2013, now abandoned.

(Continued)

(51) Int. Cl.
*A61F 2/01* (2006.01)
*A61B 17/12* (2006.01)
(Continued)

(52) U.S. Cl.
CPC .............. *A61F 2/01* (2013.01); *A61B 17/064* (2013.01); *A61B 17/1204* (2013.01); *A61B 17/12109* (2013.01); *A61B 17/12131* (2013.01); *A61B 17/12163* (2013.01); *A61B 17/12168* (2013.01); *A61B 17/12172* (2013.01); *A61B 2017/00867* (2013.01); *A61B 2017/0641* (2013.01); *A61B 2017/1205* (2013.01); *A61B 2017/2215* (2013.01); *A61F 2002/011* (2013.01); *A61F 2002/016* (2013.01); *A61F 2220/0016* (2013.01)

(58) Field of Classification Search
CPC ............................ A61B 17/12109; A61F 2/01
See application file for complete search history.

(56) References Cited

U.S. PATENT DOCUMENTS 5,527,338 A 6/1996 Purdy
6,048,331 A 4/2000 Tsugita et al.
(Continued)

FOREIGN PATENT DOCUMENTS

CN 101612052 12/2009
DE 233303 2/1986
(Continued)

OTHER PUBLICATIONS

Communication Pursuant to Rule 164(1) EPC [Supplementary Partial European Search Report] dated Feb. 5, 2016 From the European Patent Office Re. Application No. 13809443.8.
(Continued)

*Primary Examiner* — Shaun L David

(57) ABSTRACT

A blood vessel occlusion device comprising a plurality of legs having a deployed state wherein each of the plurality of legs is angled outwardly toward a vessel wall and a delivery state wherein the plurality of legs are sized and shaped for pushing into a target blood vessel and substantially in parallel to a common longitudinal axis. Each leg has an anchoring tooth at a distal end thereof and a gripping point formed therealong. Each leg switches from deployed state to delivery state by a retention element and maintained in delivery state when said retention element is supported by the gripping point.

13 Claims, 26 Drawing Sheets

Related U.S. Application Data

(60) Provisional application No. 61/722,826, filed on Nov. 6, 2012, provisional application No. 61/664,222, filed on Jun. 26, 2012.

(51) Int. Cl.
*A61B 17/064* (2006.01)
*A61B 17/00* (2006.01)
*A61B 17/221* (2006.01)

(56) References Cited

U.S. PATENT DOCUMENTS

| | | | |
|---|---|---|---|
| 6,117,157 | A | 9/2000 | Tekulve |
| 6,267,776 | B1 | 7/2001 | O'Connell |
| 6,273,901 | B1 | 8/2001 | Whitcher et al. |
| 6,419,686 | B1 | 7/2002 | McLeod et al. |
| 8,029,529 | B1 | 10/2011 | Chanduszko |
| 2002/0090389 | A1 | 7/2002 | Humes et al. |
| 2003/0195514 | A1 | 10/2003 | Trieu et al. |
| 2003/0208227 | A1 | 11/2003 | Thomas |
| 2004/0034366 | A1 | 2/2004 | Van der Burg et al. |
| 2005/0107822 | A1 | 3/2005 | WasDyke |
| 2005/0159771 | A1* | 7/2005 | Petersen .............. A61F 2/01 606/200 |
| 2006/0015144 | A1 | 1/2006 | Burbank et al. |
| 2006/0058833 | A1 | 3/2006 | VanCamp et al. |
| 2006/0287674 | A1 | 12/2006 | Ginn et al. |
| 2007/0129753 | A1 | 6/2007 | Quinn et al. |
| 2007/0173885 | A1 | 7/2007 | Cartier et al. |
| 2008/0045996 | A1 | 2/2008 | Makower et al. |
| 2008/0188887 | A1 | 8/2008 | Batiste |
| 2008/0210738 | A1 | 9/2008 | Shelton et al. |
| 2008/0221599 | A1 | 9/2008 | Starksen |
| 2009/0062838 | A1 | 3/2009 | Brumleve et al. |
| 2009/0216261 | A1 | 8/2009 | Brandeis et al. |
| 2009/0228038 | A1 | 9/2009 | Amin |
| 2009/0306703 | A1 | 12/2009 | Kashkarov et al. |
| 2010/0016881 | A1 | 1/2010 | Fleck et al. |
| 2010/0163054 | A1 | 7/2010 | Brenzel et al. |
| 2011/0196468 | A1 | 8/2011 | Brandeis |
| 2011/0213404 | A1 | 9/2011 | Binkert |
| 2011/0301630 | A1 | 12/2011 | Hendriksen et al. |
| 2012/0179172 | A1* | 7/2012 | Paul, Jr. .............. A61B 17/0057 606/142 |
| 2013/0006294 | A1 | 1/2013 | Kashkarov et al. |
| 2015/0142025 | A1 | 5/2015 | Brandeis |
| 2015/0190140 | A1 | 7/2015 | Brandeis |
| 2018/0070953 | A1 | 3/2018 | Brandeis |

FOREIGN PATENT DOCUMENTS

| | | | |
|---|---|---|---|
| DE | 102009058132 | 6/2011 | |
| EP | 1276437 | 1/2003 | |
| EP | 1878391 | 1/2008 | |
| WO | WO 99/07292 | 2/1999 | |
| WO | WO 01/72239 | 10/2001 | |
| WO | WO 03/020106 | 3/2003 | |
| WO | WO 03/079944 | 10/2003 | |
| WO | WO 2006/017470 | 2/2006 | |
| WO | WO 2008/115922 | 9/2008 | |
| WO | WO 2010/022072 | 2/2010 | |
| WO | WO-2011037866 A1 * | 3/2011 | ......... A61B 17/0057 |
| WO | WO 2014/002087 | 1/2014 | |
| WO | WO 2014/002088 | 1/2014 | |

OTHER PUBLICATIONS

International Preliminary Report on Patentability dated Jan. 8, 2015 From the International Bureau of WIPO Re. Application No. PCT/IL2013/050537.
International Preliminary Report on Patentability dated Jan. 8, 2015 From the International Bureau of WIPO Re. Application No. PCT/IL2013/050538.
International Search Report and the Written Opinion dated Oct. 15, 2013 From the International Searching Authority Re. Application No. PCT/IL2013/050538.
International Search Report and the Written Opinion dated Oct. 29, 2013 From the International Searching Authority Re. Application No. PCT/IL2013/050537.
Invitation to Pay Additional Fees dated Sep. 8, 2013 From the International Searching Authority Re. Application No. PCT/IL2013/050537.
Official Action dated Aug. 13, 2015 From the US Patent and Trademark Office Re. U.S. Appl. No. 14/411,388.
Restriction Official Action dated Jun. 2, 2015 From the US Patent and Trademark Office Re. U.S. Appl. No. 14/411,388.
Supplementary European Search Report and the European Search Opinion dated Feb. 9, 2016 From the European Patent Office Re. Application No. 13810252.0.
Communication Pursuant to Article 94(3) EPC dated Dec. 19, 2016 From the European Patent Office Re. Application No. 13810252.0. (5 Pages).
Supplementary European Search Report and the European Search Opinion dated Jun. 20, 2016 From the European Patent Office Re. Application No. 13809443.8.
Restriction Official Action dated Feb. 13, 2017 From the US Patent and Trademark Office Re. U.S. Appl. No. 14/411,389. (10 pages).
Communication Purusant to Article 94(3) EPC dated May 11, 2017 From the European Patent Office Re. Application No. 13810252.0. (5 Pages).
Official Action dated Jun. 15, 2017 From the US Patent and Trademark Office Re. U.S. Appl. No. 14/411,389. (33 Pages).
Official Action dated Nov. 1, 2019 From the US Patent and Trademark Office Re. U.S. Appl. No. 15/813,356. (24 Pages).

* cited by examiner

VESSEL OCCLUSION DEVICES, KITS AND METHODS

RELATED APPLICATIONS

This application is a division of U.S. patent application Ser. No. 14/411,388 filed on Dec. 25, 2014, which is a National Phase of PCT Patent Application No. PCT/IL2013/050537 having International filing date of Jun. 25, 2013, which claims the benefit of priority of U.S. Provisional Patent Application Nos. 61/664,222 filed on Jun. 26, 2012 and 61/722,826 filed on Nov. 6, 2012. The contents of the above applications are all incorporated by reference as if fully set forth herein in their entirety.

FIELD AND BACKGROUND OF THE INVENTION

The present invention, in some embodiments thereof, relates to blood vessel treatment and, more particularly, but not exclusively, to expandable devices and methods for blood vessel occlusion.

A malfunction in the ability of veins or arteries to supply or remove blood is associated with medical conditions such as varicose vein expansion, aneurysms and tumors.

Varicose veins appear in 20-25% of women and 10-15% of men. Most varicose veins are considered a cosmetic condition rather than a medical condition; however, in some cases, hindered circulation may cause pain, disfiguring, swelling, discomfort, a tingling sensation, itching and/or a feeling of heaviness.

Several techniques and procedures to treat varicose veins exist. Vein stripping involves tying off of the upper end of a vein and then removing the vein. Vein stripping is typically performed in an operating room under general anesthesia. Approximately 150,000 vein stripping surgeries are performed each year in the U.S. Vein stripping associated risks include risks linked to general anesthesia such as anesthesia allergies, infections etc. In addition, tissue around the stripped vein may become bruised and scarred causing a feeling of "tightness" in the leg. Damaged may cause numbness and paralysis of part of the leg.

Endovenous laser treatment is typically performed done in-office under local anesthesia. Endovenous laser treatment uses intense heat to remove a vein, which may lead to an increased risk of developing blood clots. Treated veins can also become irritated and inflamed, leading to pain and swelling in the legs. The treated area can begin to tingle or become burned from the heat.

Radiofrequency occlusion is typically performed done in-office under local anesthesia or in an ambulatory surgery setting. A small tube or catheter is used and threaded along the vein using ultrasound guidance. Local anesthetic is injected along the way to help ensure the patient's comfort throughout the procedure. Once the vein is canalized, sound waves are applied to heat and collapse the vein from the top, down. The vein will eventually result in a thin scar tissue and is absorbed by the body's natural processes. Following treatment with radiofrequency occlusion, a compression bandage is applied to the leg to aid in the healing process. This should be kept in place for a couple of days and then compression stockings are worn for another two to three weeks to continue to aid the healing process. Patients may walk shortly after treatment and most are able to resume normal activities or return to work after a few days provided they avoid heavy lifting and wear their compression stockings. There may be a chance of bleeding, infection or blood clots with radiofrequency occlusion as with many other procedures. A unique complication that is associated with radiofrequency occlusion, however, is skin burn due to the method of occlusion used during treatment.

Ultrasound-guided sclerotherapy is typically performed done in-office under local anesthesia. Side effects that are applicable for standard sclerotherapy are also applicable to ultrasound-guided sclerotherapy, although the magnitude of certain complications, when they occur, may be greater. Standard sclerotherapy side effects include skin ulceration or necrosis, deep vein thrombosis, allergic reaction, arterial injection, pulmonary embolus, nerve injury, wound breakdown and wound inflammation.

SUMMARY OF THE INVENTION

According to an aspect of some embodiments of the present invention there is provided a blood vessel occlusion device comprising: a plurality of legs having a deployed state wherein each of the plurality of legs is angled outwardly toward a vessel wall and a delivery state wherein the plurality of legs are sized and shaped for pushing into a target blood vessel and substantially in parallel to a common longitudinal axis, each the leg having an anchoring tooth at a distal end thereof and a gripping point formed therealong; wherein each of the leg switches from the deployed state to the delivery state by a retention element and maintained in the delivery state when the retention element is supported by the gripping point.

Optionally the retention element is common to the plurality gripping points. Optionally, the blood vessel occlusion device further comprises a plurality of retention elements. Optionally, the blood vessel occlusion device further comprises a common base wherein the plurality of legs connects to the common base. Optionally, the angle between the plurality of legs is bigger in the deployed state than in the delivery state. Optionally, the gripping point is an essentially closed hook and the retention element is a pulling wire intertwined in the closed hooks. Optionally, the gripping point is a projection and the retention element is a moveable ring and the moveable ring can be held constantly by the projections. Optionally, the blood vessel occlusion device has a front side and a back side and the vessel occlusion device further comprises a ring pushing element behind the moveable ring. Optionally, the delivery state fits a deployment device. Optionally, the plurality of legs is made of a shape memory alloy.

According to an aspect of some embodiments of the present invention there is provided a blood vessel occlusion device comprising: a plurality of legs having a deployed state wherein each of the plurality of legs is angled outwardly toward a vessel wall and a delivery state wherein the plurality of legs are sized and shaped to curve along the blood vessel and substantially in parallel to a common longitudinal axis, each the leg having an anchoring tooth at a distal end thereof.

Optionally, each the leg switches from the deployed state to the delivery state by a retention element. Optionally, the plurality of legs is made of a shape memory alloy.

According to an aspect of some embodiments of the present invention there is provided a blood vessel occlusion device comprising a plurality of expandable spiral wires, wherein the plurality of expandable spiral wires expand upon release from a deployment device to grasp blood vessel walls.

Optionally, rotation of the at least one expandable spiral wires narrows the blood vessel thereby occluding the blood vessel. Optionally, the blood vessel occlusion device further comprises a retention element which maintains the rotation. Optionally, occlusion is achieved by rotating the plurality of expandable spiral wires. Optionally, at least one the expandable spiral wire is a right handed spiral and at least one the expandable spiral wire is a left handed spiral. Optionally, the blood vessel occlusion further comprises a retention element which rotates the at least one expandable spiral wires thereby narrowing the blood vessel. Optionally, the blood vessel occlusion further comprises at least one gripping point wherein the blood vessel is maintained narrow when the retention element is supported by the gripping points. Optionally, the expandable spiral wires are made of a shape memory alloy.

According to an aspect of some embodiments of the present invention there is provided a blood vessel occlusion device, comprising: an expandable proximal ring having a proximal outer radial surface and a plurality of anchoring teeth therealong; an expandable distal ring having a distal outer radial surface and a plurality of anchoring teeth therealong; and a constriction mechanism; wherein the plurality of anchoring teeth are capable of grasping a vein's wall and the constriction mechanism constrains torsion movement of the expandable proximal ring relative to the expandable distal ring.

Optionally, the blood vessel occlusion device further comprises a deployment device. Optionally, the blood vessel occlusion device further comprises a pushing element wherein the deployment device has a lumen and the pushing element fits into the lumen. Optionally, the blood vessel occlusion device further comprises a blood clot cage essentially distal to the expandable distal ring. Optionally, the expandable proximal ring and the expandable distal ring are made of a shape memory alloy.

According to an aspect of some embodiments of the present invention there is provided a blood vessel occlusion device, comprising: a first expandable annular element having a plurality of anchoring teeth having a delivery state wherein each anchoring tooth is angled outwardly and a deployed state mode wherein the first expandable annular element is sized and shaped for being placed in a target blood vessel and wherein each the anchoring tooth is substantially aligned along a common longitudinal axis; and a second expandable annular element having a delivery state wherein the second expandable annular element contacts a vessel wall and a deployed state wherein the second expandable annular element is sized and shaped for pushing into a target blood vessel; wherein the width of the second expandable annular element is bigger than the width of the first expandable annular element and the tip of each of the plurality of anchoring teeth faces the second expandable annular element when the plurality of anchoring teeth and the second annular element are in the delivery state.

Optionally, the second annular element presses against blood vessel walls thereby securing the device the blood vessel. Optionally, the blood vessel occlusion device further comprises a retention element essentially encircling the first expandable annular element. Optionally, the blood vessel occlusion device further comprises a groove between the first expandable annular element and the second expandable annular element wherein the groove supports the retention element. Optionally, the first expandable annular element and the second expandable annular element are made of a shape memory alloy.

According to an aspect of some embodiments of the present invention there is provided a blood vessel occlusion device, comprising: an expandable tubular frame having a lower end and an upper end; and an expandable ring encircling the upper end having a deployed state wherein the expandable ring essentially occupies a target blood vessel lumen and a delivery state wherein the expandable ring and the expandable tubular frame are sized and shaped for pushing into a target blood vessel; wherein the expandable ring is essentially perpendicular to the expandable tubular frame.

Optionally, the blood vessel occlusion device further comprises a retention element encircling the tubular frame wherein the retention limit the width of the expandable ring and shortens the distance between the lower end of the expandable tubular frame and upper end of the expandable ring. Optionally, the blood vessel occlusion device has a front side and a back side and the blood vessel occlusion device further comprises a blood clot cage essentially in front of the plurality of the expandable ring. Optionally, the blood vessel occlusion device further comprises an upper anchoring element mounted on the expandable ring; and a lower anchoring element mounted on the expandable tubular frame; wherein the upper and lower anchoring elements are capable of grasping a blood vessel wall. Optionally, the upper anchoring element is a plurality of anchoring teeth and the lower anchoring element is a plurality of anchoring teeth. Optionally, the expandable tubular frame has an interior side and an exterior side and upon pulling the expandable ring towards the lower end the expandable ring creates a funnel shape at the interior side thereby changing the position of the upper anchoring element. Optionally, the expandable tubular frame and the expandable ring are made of a shape memory alloy.

According to an aspect of some embodiments of the present invention there is provided a blood vessel occlusion device, comprising: an expandable sleeve having an inner side, an outer side; a plurality of anchoring teeth on the outer side; a pulling wire attached to the expandable sleeve; and a retention element positioned to wrap around the expandable sleeve; wherein the expandable sleeve have an unturned mode and a turned mode, when the outer side faces outside of the expandable sleeve when in unturned mode and faces inside of the expandable sleeve when in turned mode and the pulling wire is capable of transforming the expandable sleeve from unturned mode to turned mode by flipping the expandable sleeve inside out and the plurality of projections are capable of grasping a vein's wall and the retention element restricts the dimensions of the expandable sleeve.

Optionally, the expandable sleeve has a front side and a rear side and the retention element is positioned at the rear side. Optionally, the expandable sleeve is thermally treated. Optionally, the blood vessel occlusion device further comprises a deployment device which limits the expansion of the expandable sleeve and is capable of delivering the blood vessel occlusion device to a target blood vessel. Optionally, the blood vessel occlusion device further comprises a blood clot cage essentially in front of the front side. Optionally, the expandable sleeve is made of a shape memory alloy.

According to an aspect of some embodiments of the present invention there is provided a method for occluding a blood vessel comprising: inserting a deployment device carrying an expandable element and a constriction element into a target blood vessel; moving the deployment device with respect to the expandable element thereby releasing top part of the expandable element and allowing the expandable element to attach to a blood vessel wall; moving the constricting element with respect to the expandable element thereby narrowing the expandable element; and moving the deployment device with respect to the expandable element thereby releasing bottom part of the expandable element allowing the expandable element to self stabilize against vessel wall.

Optionally, the method further comprises removing the deployment device from the target blood vessel. Optionally, the method further comprises delivering an occluding agent. Optionally, the method further comprises rotating the expandable element after the releasing top part.

According to an aspect of some embodiments of the present invention there is provided a method for occluding a blood vessel comprising: inserting a deployment device carrying an expandable spiral element into a target blood vessel; moving the deployment device with respect to the expandable spiral element thereby releasing the expandable spiral element and allowing the expandable spiral element to attach to a blood vessel wall; and constricting expandable spiral element.

Optionally, constriction is performed by rotating the expandable spiral element thereby occluding the blood vessel. Optionally, the method further comprises removing the deployment element.

According to an aspect of some embodiments of the present invention there is provided a method for occluding a blood vessel comprising: inserting a deployment device carrying an expandable proximal ring and an expandable distal ring into a target blood vessel; moving the deployment device with respect to the expandable distal ring thereby releasing the expandable distal ring and attaching the expandable distal ring to a target blood vessel wall; rotating the expandable distal ring to constrict the target blood vessel wall; moving the deployment device with respect to the expandable proximal ring thereby releasing the expandable proximal ring and attaching the expandable proximal ring to a target blood vessel wall; rotating the expandable proximal ring to constrict the target blood vessel wall; and constricting torsion movement of the expandable proximal ring with respect to the expandable distal ring; wherein the target blood vessel is occluded by the rotation of the expandable distal ring and rotation of the expandable proximal ring.

Optionally, rotation of the expandable distal ring is in counter direction with respect to rotation of the expandable proximal ring. Optionally, the method further comprises removing the deployment device from the target blood vessel. Optionally, the method further comprises releasing an occluding agent.

According to an aspect of some embodiments of the present invention there is provided a method for occluding a blood vessel comprising: inserting a deployment device carrying an expandable sleeve and a constriction element into a target blood vessel; moving the deployment device with respect to the expandable sleeve thereby releasing top part of the expandable sleeve and allowing the expandable sleeve to attach to a blood vessel wall; flipping the expandable sleeve inside out; and moving the constricting element with respect to the expandable sleeve thereby narrowing the expandable sleeve.

Optionally, the method further comprises removing the deployment device from the target blood vessel. Optionally, the method further comprises releasing an occluding agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to blood vessel treatment and, more particularly, but not exclusively, to expandable devices and methods for blood vessel occlusion.

Figure 1:
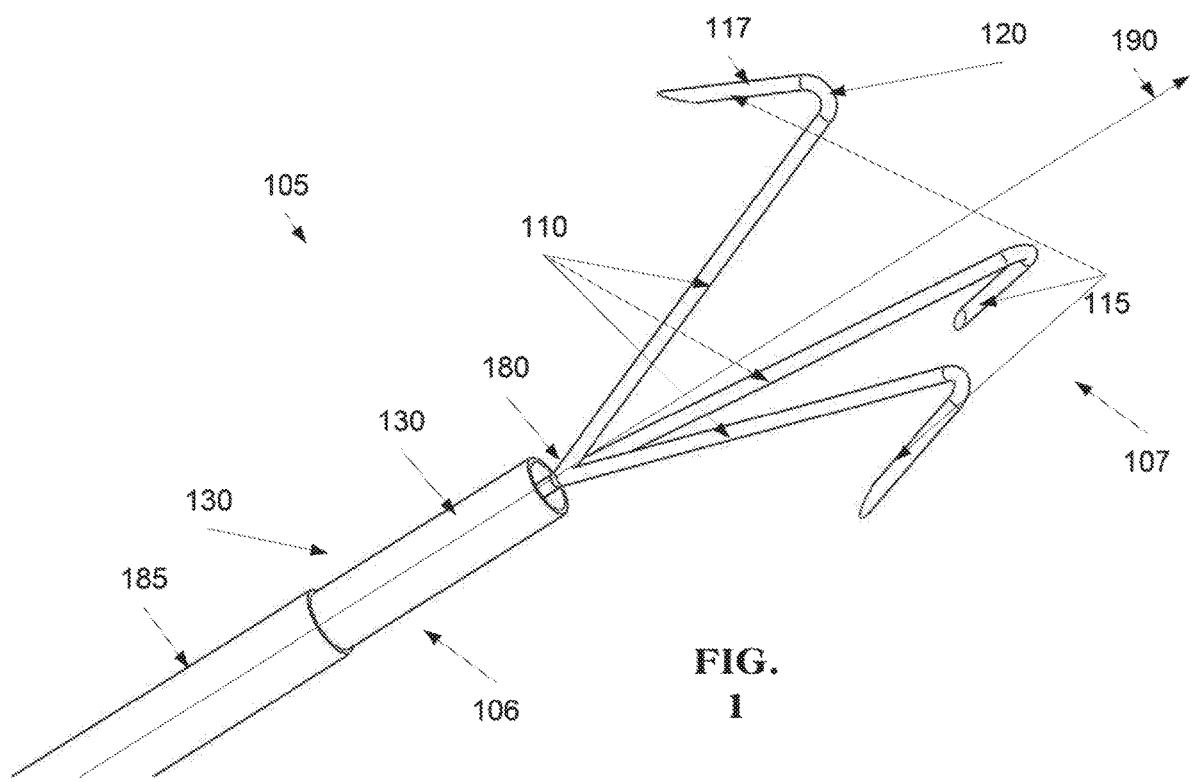
FIG. 1 is a schematic illustration of a blood vessel occlusion device having three legs in a deployed state, a common rear base and a annular retention element, according to some embodiments of the present invention.

Referring now to the drawings, FIG. 1 is a 3D schematic illustration of a blood vessel occlusion device 105 having three legs 110 in a deployed state, a common rear base 180 and an annular retention element 130, according to some embodiments of the present invention. The legs 110, which are depicted in a deployed state, are angled outwardly 120 toward a vessel wall, away from the common longitudinal axis 190. Optionally, the legs 110 are made of a shape memory alloy (SMA) comprising copper-aluminium-nickel, nickel-titanium, zinc alloy, copper alloy, gold alloy and/or iron alloy. The SMA may be reversibly deformed and/or irreversibly deformed. During the deployment process, the legs 110 protrude and/or penetrate a blood vessel wall to anchor the vessel occlusion device 105 in place. In a deployed state, the legs 110 are angularly positioned to be closer to each other at the rear side 106 than at the front side 107. The common base 180 may be straight and/or curved. The common base 180 may be connected to the legs 110 close to their rear tips and/or along the legs 110. At the distal end 117 of each leg 110 is an anchoring tooth 115. Optionally, a single leg 110 has multiple anchoring teeth 115. The anchoring teeth 115 may be positioned along the leg 110 and/or at the leg's distal end 117. The anchoring teeth 115 may be cut and/or sharp to enable gripping a blood vessel wall. The anchoring teeth 115 tips may be angled up and/or down. Optionally, a plurality of cuts and/or tip shapes is provided for a single tooth 115. The anchoring teeth 115 may be angularly connected 120 to the legs 110. This angle may assist in gripping a blood vessel wall. Optionally, the legs 110 and anchoring teeth 115 are parts of a single unit of a shape memory alloy (SMA) The retention element 130 may be a ring, for example a cylindrical element shaped as a short tube. In use, in order to load the vessel occlusion device 105 into a catheter, the ring 130 is moved over the legs 110 to pull them toward each other and/or toward the common longitudinal axis 190. The ring maintains the vessel occlusion device 105 in a delivery state where the legs 110 are substantially parallel to the common longitudinal axis 190. The legs 110 are sized and shaped to curve along the natural curves of a target blood vessel. A shape fitting for curving along a blood vessel may be achieved in a delivery state. The blood vessel occlusion device 105 may be held in a delivery state by a deployment device 185. In order to switch from the deployed state to the delivery state, after the anchoring teeth 115 is stabbed into the vessel wall, the legs 110 are pulled by the movement of the retention element 130 in relation to the vessel occlusion device 105. The movement of the retention element 130 may be essentially parallel to the common longitudinal axis 190. Optionally, the movement of the retention element along the legs 110 may be achieved by keeping the retention element essentially constant and moving the legs 110. The pulling of the stabbed legs contracts the blood vessel, optionally to an extent that occludes the target blood vessel.

Figure 2:
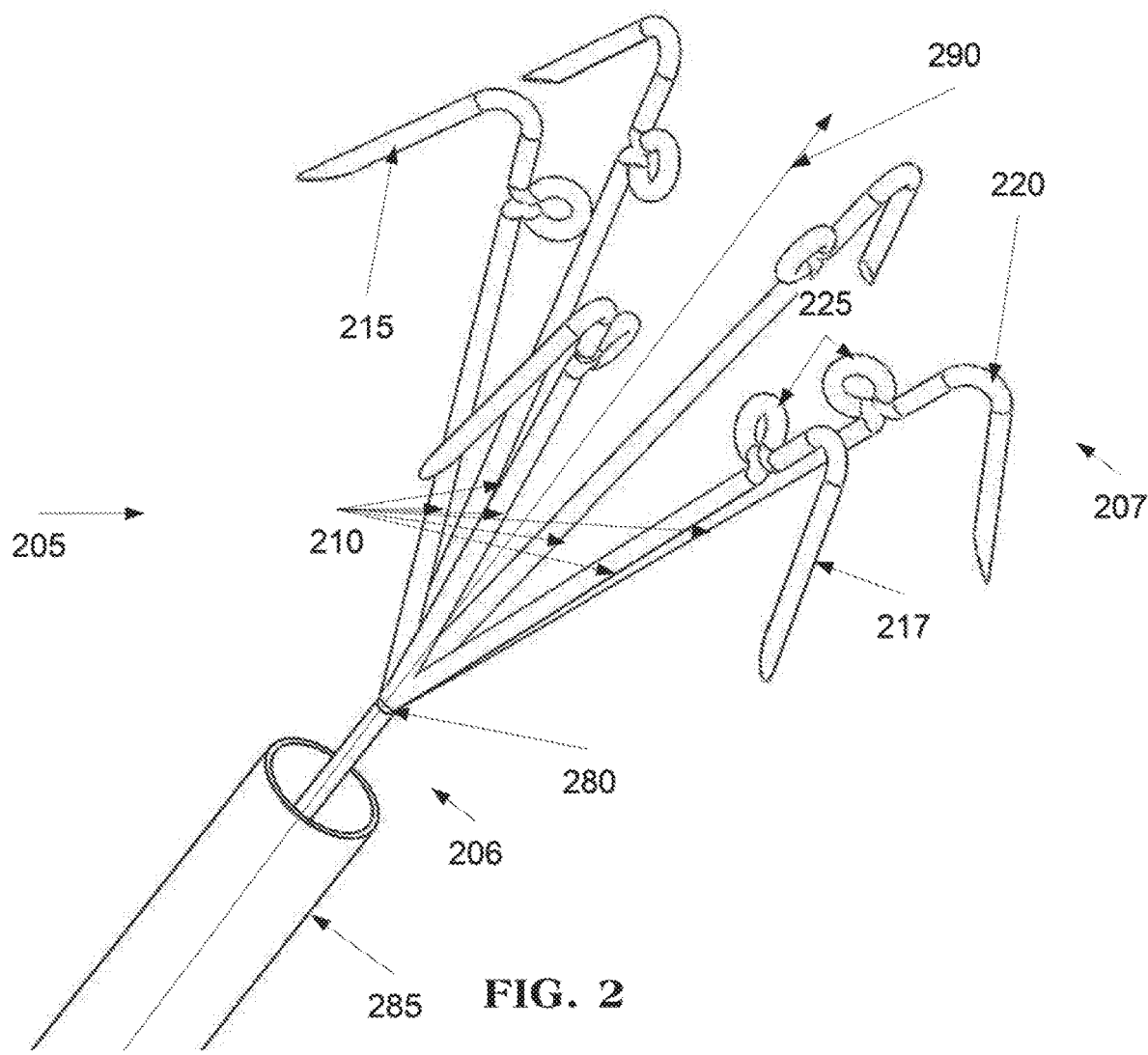
FIG. 2 is a schematic illustration of a blood vessel occlusion device having six legs in a deployed state, a common rear base and essentially circular hooks, according to some embodiments of the present invention.

Reference is now made to FIG. 2, which is a 3D schematic illustration of a blood vessel occlusion device 205 having six legs 210 in a deployed state, a common rear base 280 and essentially circular hooks, according to some embodiments of the present invention. The legs 210, which are depicted in a deployed state, are angled outwardly 220 toward a vessel wall, away from the common longitudinal axis 290 as depicted in FIG. 1. The legs 210 are angularly positioned to be closer to each other at the rear side 206 than at the front side 207. At the distal end 217 of each leg 210 has an anchoring tooth 215. The anchoring teeth's 215 tips may be cut and/or sharp to enable gripping a blood vessel wall. The anchoring teeth 215 may be angularly connected 220 to the legs 210. This angle may assist in gripping a blood vessel wall. The gripping point 225 may be, for example, an essentially circular hook. The retention element may be, for example, a pulling wire. The circular hook 225 may have a small opening for intertwining a pulling wire. An action of pulling the pulling wire when it is intertwined with the circular hooks 225 results in bringing the legs 210 closer to each other and/or to the common longitudinal axis 290. The movement of the pulling wire may be essentially parallel to the common longitudinal axis 290. The anchoring teeth 215 may pull along the blood vessel walls thereby narrowing the blood vessel and/or occluding the blood vessel. In a delivery state the legs 210 are parallel to the common longitudinal axis 290. A shape fitting for curving along a blood vessel may be achieved in a delivery state. In order to facilitate the insertion of the blood vessel occlusion device 205 into a target blood vessel, the blood vessel occlusion device 205 is held in the delivery state by a deployment device 285. Optionally, the blood vessel occlusion device 205 is held in the delivery state by the retention element 230 such as a circular hook and/or a pulling wire and/or an additional retention element other then the retention element 230 used to pull the legs 210. The deployment device 285, may be a catheter and/or a syringe.

Figure 3:
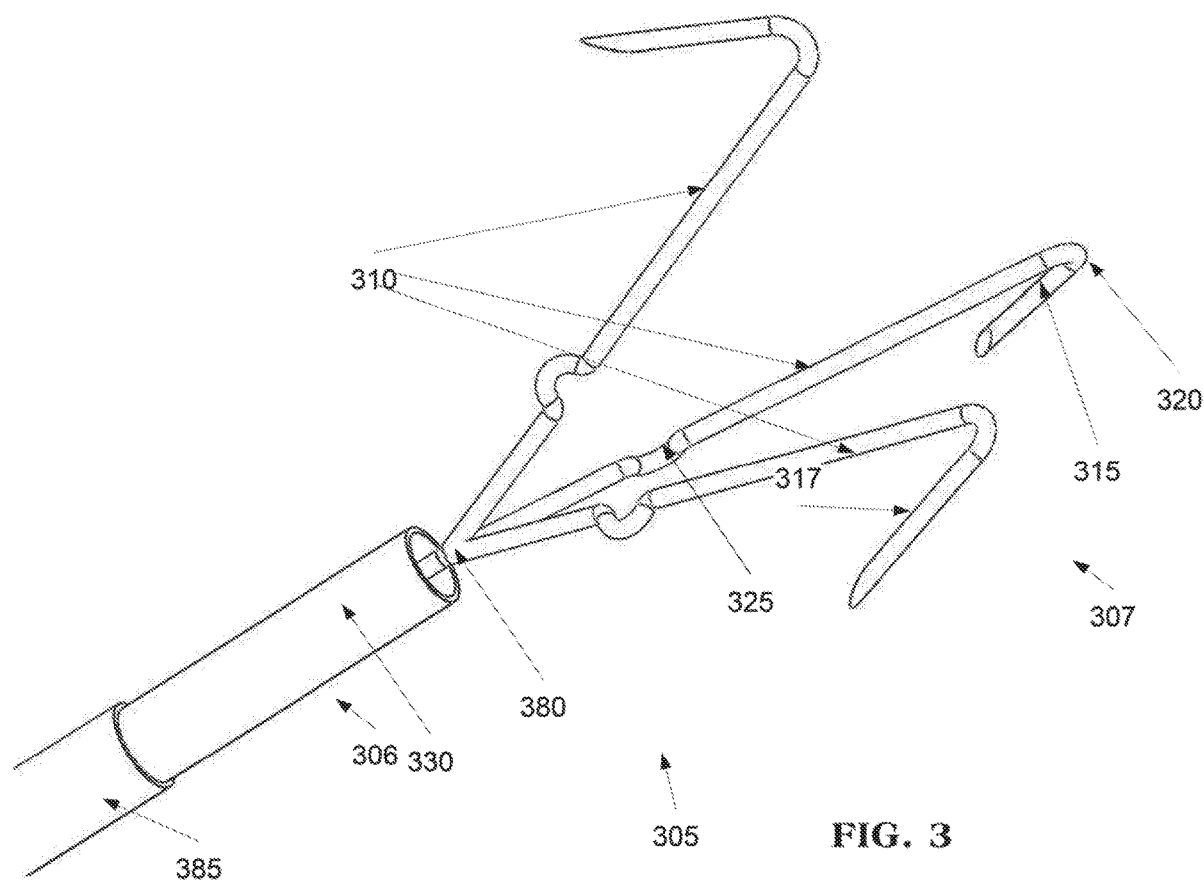
FIG. 3 is a schematic illustration of a blood vessel occlusion device having three legs with projections in a deployed state, a common rear base, projections and a annular retention element, according to some embodiments of the present invention.

Reference is now made to FIG. 3, which is a 3D schematic illustration of a blood vessel occlusion device 305 having three legs with projections 325 in a deployed state, a common rear base 380, projections 325 and an annular retention element 330, according to some embodiments of the present invention. The blood vessel occlusion device 305 is as described for FIG. 1, with a corresponding numbering scheme. Here each leg 310 further comprises a projection 325. In use, the retention element 330 may be pushed over the projections 325 and anchored by them so as to maintain the blood vessel occlusion device 305 in a delivery state.

Figure 4:
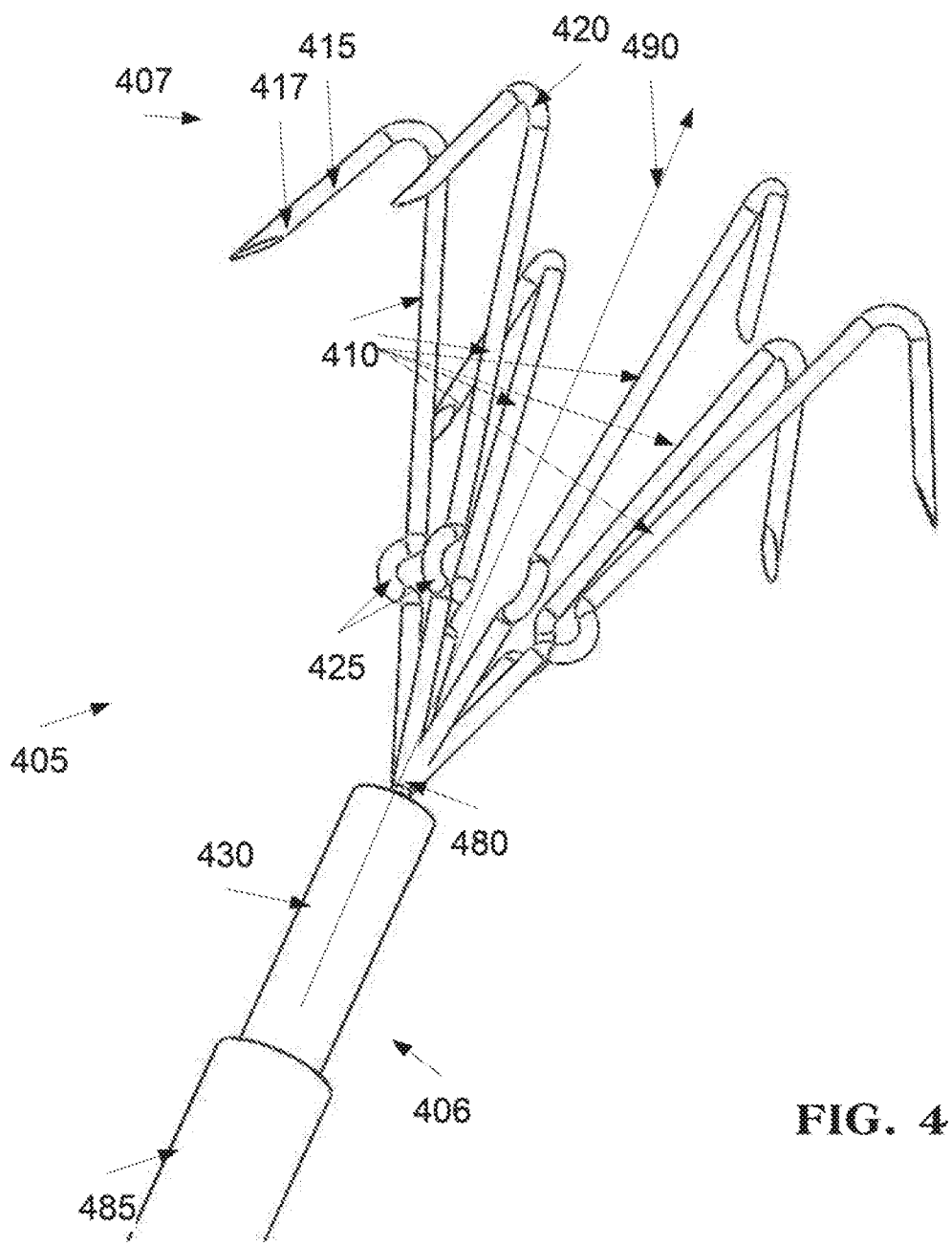
FIG. 4 is a schematic illustration of a blood vessel occlusion device having six legs in a deployed state, a common rear base, projections and a annular retention element, according to some embodiments of the present invention.

Reference is now made to FIG. 4, which is a 3D schematic illustration of a blood vessel occlusion device 405 having six legs 410 in a deployed state, a common rear base 480, projections 425 and an annular retention element 430, according to some embodiments of the present invention. The blood vessel occlusion device is as described for FIG. 3 having six legs 410 instead of three legs 310. The numbering scheme corresponds to the numbering scheme of FIG. 3.

Figure 5:
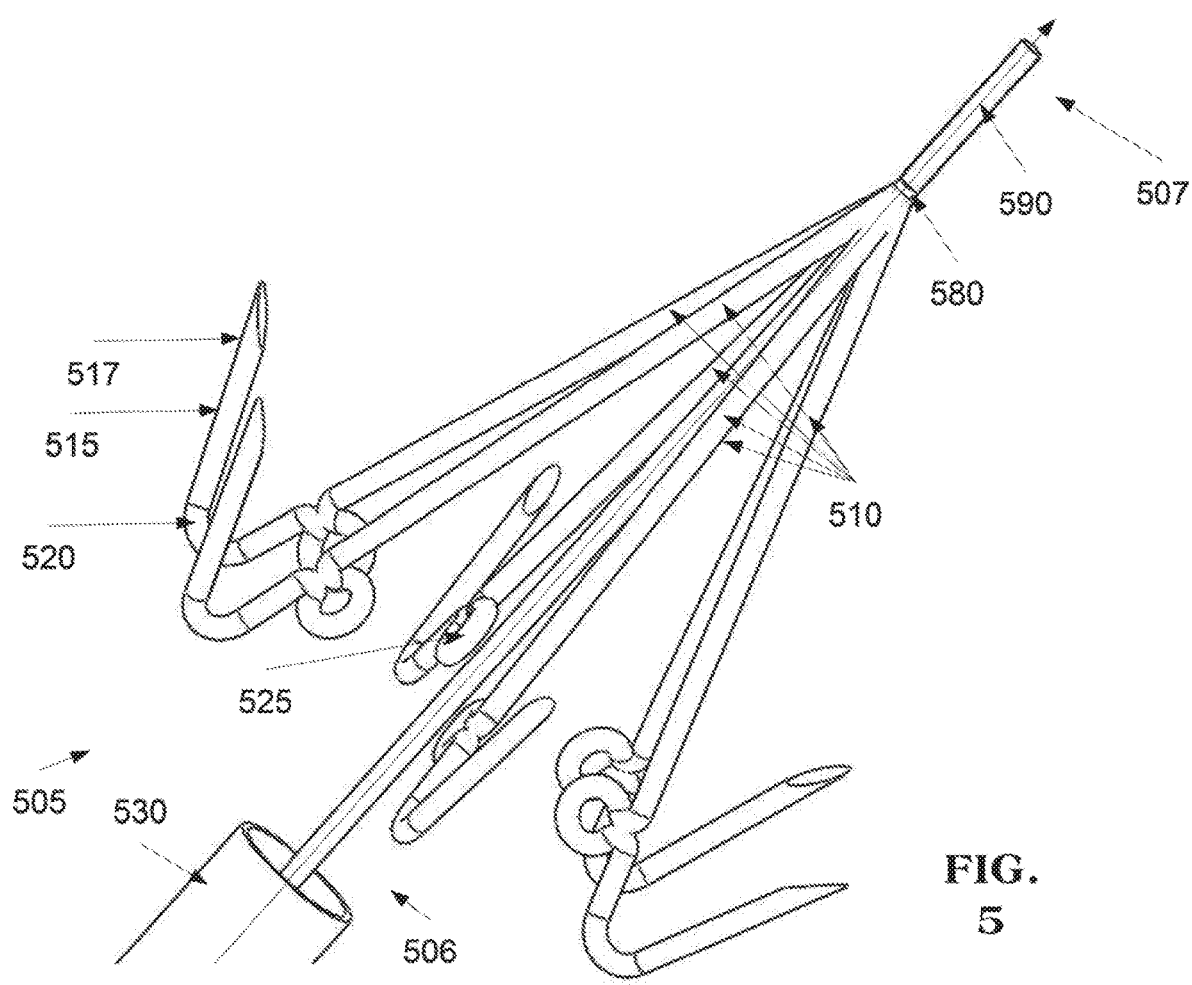
FIG. 5 is a schematic illustration of a blood vessel occlusion device having six legs in a deployed state, a common front base and essentially circular hooks, according to some embodiments of the present invention.

Reference is now made to FIG. 5, which is a 3D schematic illustration of a blood vessel occlusion device 505 having six legs 510 in a deployed state, a common front base 580 and essentially circular hooks 525, according to some embodiments of the present invention. The blood vessel occlusion device is as described in FIG. 2. Here the legs 510 are angularly positioned to be closer to each other at the front side of the blood vessel occlusion device 507 than at the rear side of the blood vessel occlusion device 506. The numbering scheme corresponds to the numbering scheme of FIG. 2.

Figure 6:
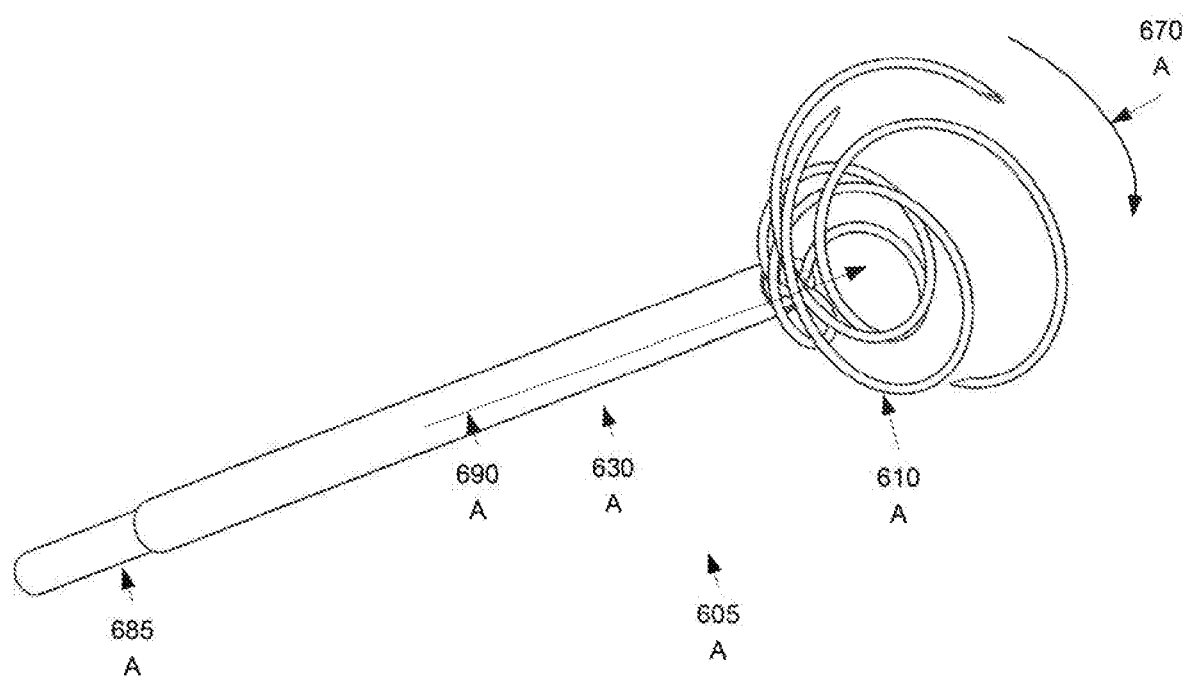
FIG. 6A is a schematic front view illustration of a blood vessel occlusion device having three expandable spiral wires, according to some embodiments of the present invention.
FIG. 6B is a schematic side view illustration of a blood vessel occlusion device having three expandable spiral wires, according to some embodiments of the present invention.
FIG. 6C is a schematic illustration of side view of a blood vessel occlusion device having expandable proximal and distal rings with a plurality of anchoring teeth on their outer radial surface, according to some embodiments of the present invention.
FIG. 6D is a three dimensional (3D) schematic side view of a blood vessel occlusion device having expandable proximal and distal rings with a plurality of anchoring teeth on their outer radial surface, according to some embodiments of the present invention.
Figure 6:
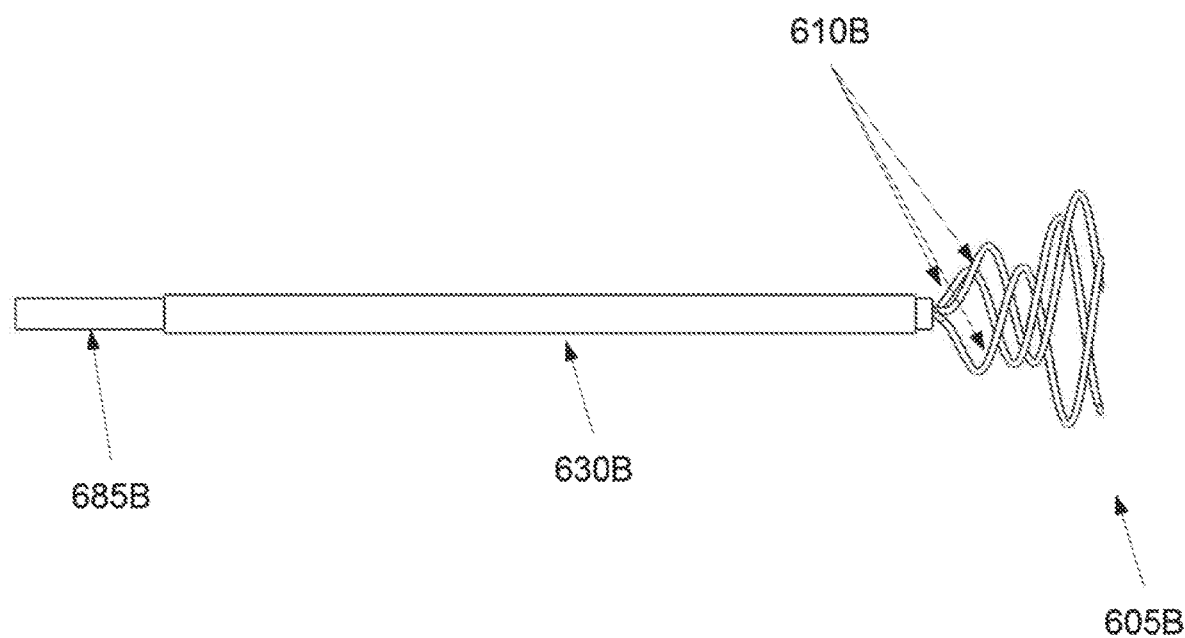
Figure 6:
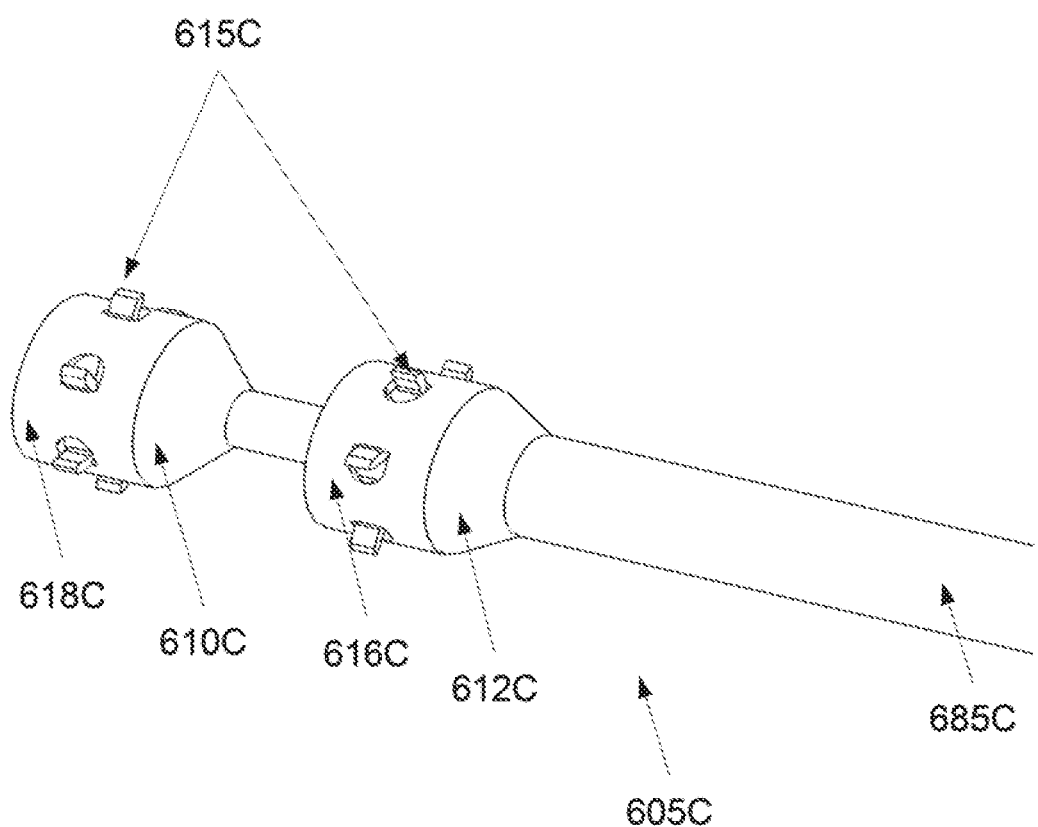
Figure 6:
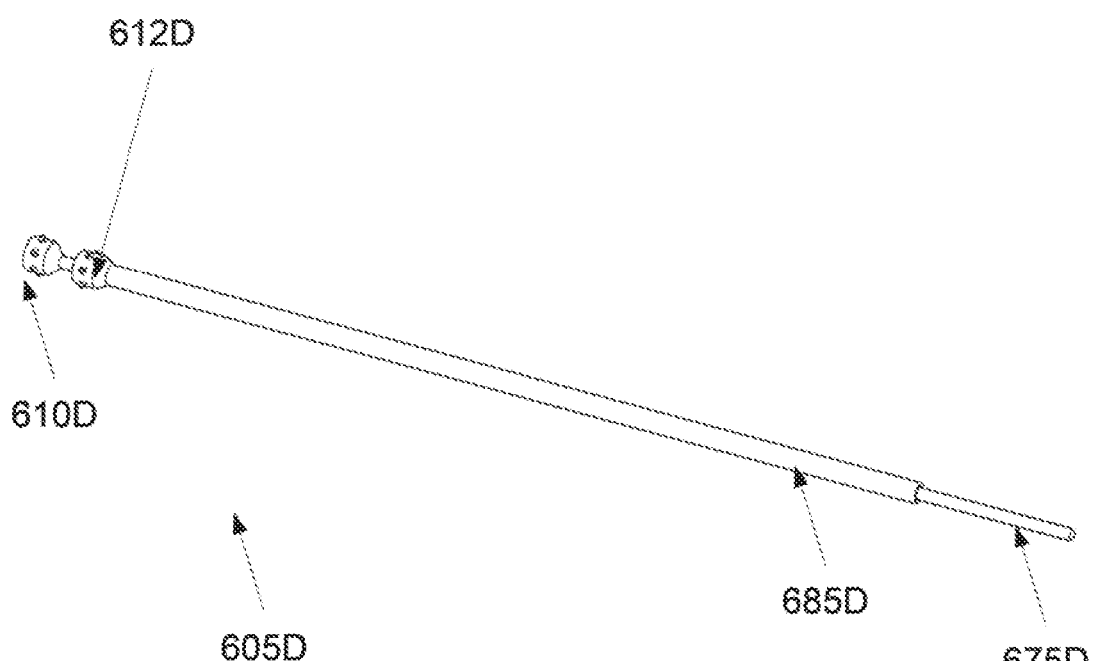

Reference is now made to FIG. 6A, which illustrates the 3D schematic front view of a blood vessel occlusion device 605A having three expandable spiral wires 610A, according to some embodiments of the present invention. The expandable spiral wires may be right handed and/or left handed. Optionally, the expandable spiral wire 610A is made of a shape memory alloy (SMA) comprising copper-aluminium-nickel, nickel-titanium, zinc alloy, copper alloy, gold alloy and/or iron alloy. The SMA may be reversibly deformed and/or irreversibly deformed. The blood vessel occlusion device 605A may have a retention element 630A. The retention element 630A may be, for example, a ring. The ring 630A slides over the expandable spiral wires 610A to pull the expandable spiral wires 610A closer to each other and/or to a common longitudinal axis 690A. The movement of ring 630A over the expandable spiral wires 610A may be a result of the ring 630A and/or the expandable spiral wires 610 changing location. The expandable spiral wires 610A may expand upon release from a deployment device 685A to grasp a blood vessel's walls. The blood vessel occlusion device 605A is sized and shaped to curve along a blood vessel. A shape fitting for curving along a blood vessel may be achieved in a retained and/or a deployed mode. Rotation of the expandable spiral wires 610A may narrow a blood vessel thereby occluding the blood vessel. The rotation may be achieved in part and/or in whole by the retention element 630A which rotates at least one expandable spiral wire 610A. The blood vessel occlusion device 610A may further have at least one gripping point to support the retention element 630A and maintain the blood vessel occlusion device 605A in a retained configuration.

Reference is now made to FIG. 6B, which illustrates the 3D schematic side view of a blood vessel occlusion device 605B having three expandable spiral wires 610B, according to some embodiments of the present invention. The blood vessel occlusion device is as depicted and described in FIG. 6A.

Reference is now made to FIG. 6C, which illustrates the 3D schematic side view of a blood vessel occlusion device 605C having expandable proximal 612C and distal 610C rings with a plurality of anchoring teeth on their outer radial surface, according to some embodiments of the present invention. The blood vessel occlusion device 605C is comprised of expandable proximal 612C and distal rings 610C. Each expandable ring 610C, 612C has a plurality of anchoring teeth 615C along its distal outer radial surface 616C, 618C. The plurality of anchoring teeth 615 C is capable of grasping a vein's wall. The constriction mechanism constrains torsion movement of the expandable proximal ring 612C relative to said expandable distal ring 610C. Optionally, expandable proximal and distal rings 610C, 612C are made of a shape memory alloy (SMA) comprising copper-aluminium-nickel, nickel-titanium, zinc alloy, copper alloy, gold alloy and/or iron alloy. The SMA may be reversibly deformed and/or irreversibly deformed.

Reference is now made to FIG. 6D, which illustrates the 3D schematic side view of a blood vessel occlusion device 605D having expandable proximal and distal rings with a plurality of anchoring teeth on their outer radial surface and a pushing element 675D, according to some embodiments of the present invention. The blood vessel occlusion device 605D is as depicted in FIG. 6C.

Figure 7:
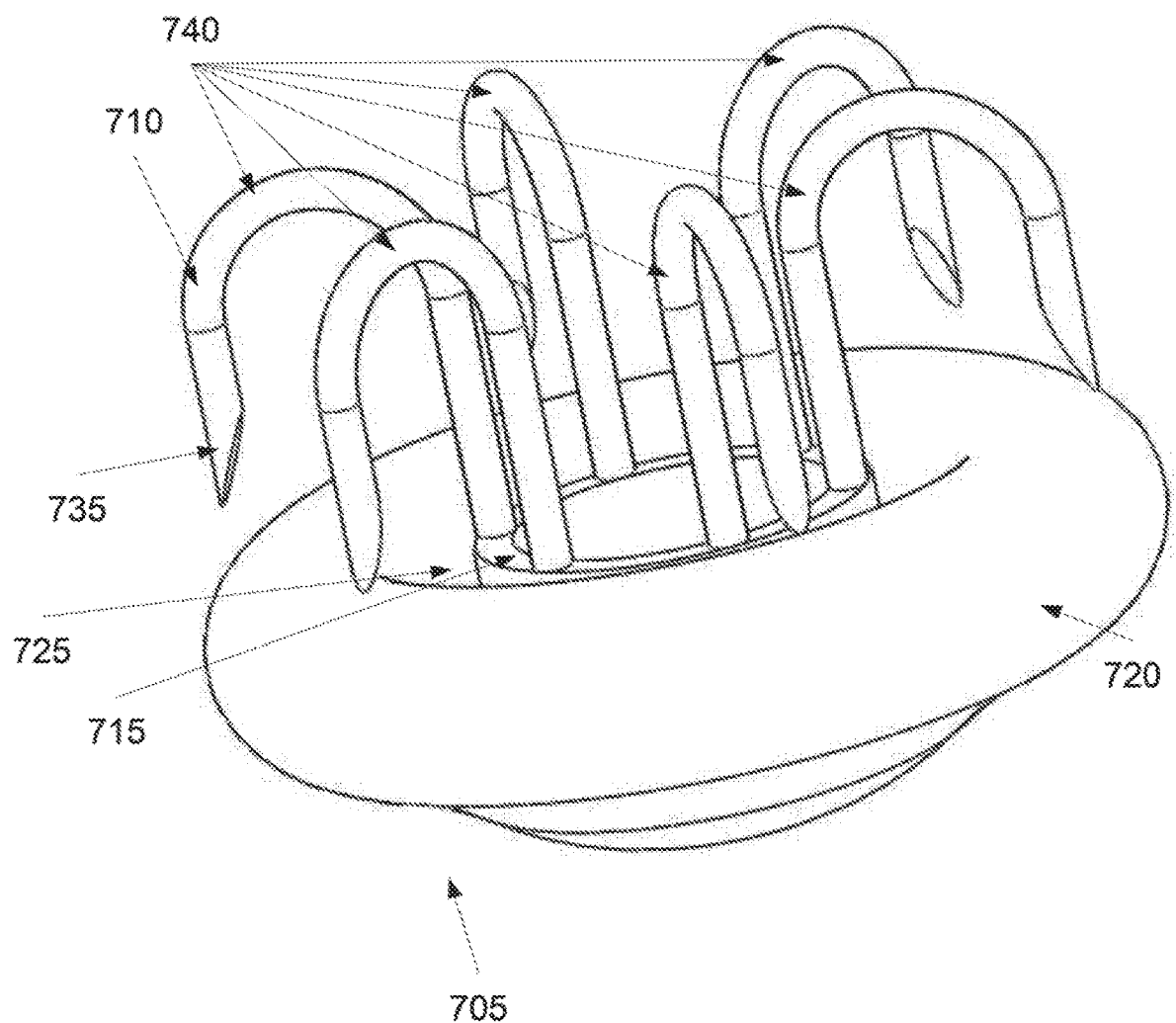
FIG. 7 is a 3D schematic illustration of a blood vessel occlusion device having a first and second expandable annular elements in deployed state and a plurality of anchoring teeth, according to some embodiments of the present invention.

Reference is now made to FIG. 7, which is a 3D schematic illustration of a blood vessel occlusion device 705 having first 715 and second 720 expandable annular elements in deployed state and a plurality of anchoring teeth 210, according to some embodiments of the present invention. The blood vessel occlusion device 705 comprises two expandable annular elements: first 715 and second 720. Optionally, there is a groove 725 between the first expandable annular element 715 and said second expandable annular element 720. The groove 725 may support a retention element. The first expandable annular element 715 has a plurality of anchoring teeth 710. The teeth 710 may be angularly mounted 740 on the first expandable annular element 715. The teeth 710 may be sharpened to penetrate a blood vessel wall when bended therethrough. The first expandable annular element 715 has two states: a delivery state and a deployed state. In a deployed state each anchoring tooth 710 is angled outwardly. In a deployed state the first expandable annular element 710 is sized and shaped for being placed in a target blood vessel. In the deployed state each anchoring tooth 710 is substantially aligned along a common longitudinal axis. The second expandable annular element 720 also has two states: a delivery state and a deployed state. In its deployed state the second expandable annular element 720 contacts a vessel wall. The second annular element 720 may apply pressure on the blood vessel walls in its deployed state. The pressure may secure the blood vessel occlusion device 705 to the blood vessel. The closing gap between the first expandable annular element 715 and the tips 735 may further secure the blood vessel occlusion device 705 to the blood vessel. In its delivery state, the second expandable annular element 720 is sized and shaped for pushing into a target blood vessel. The width of the second expandable annular element 720 is bigger than the width of the first expandable annular element 715. The second expandable annular element 720 may encircle the first expandable annular element 715. The tip 735 of each of the plurality of anchoring teeth 710 faces the second expandable annular element 720 when the teeth 710 and the second annular element 720 are in their deployed state. The blood vessel occlusion device 705 may grasp a blood vessel wall between its anchoring teeth 710 and the second expandable annular element 720 when in deployed state.

Figure 8:
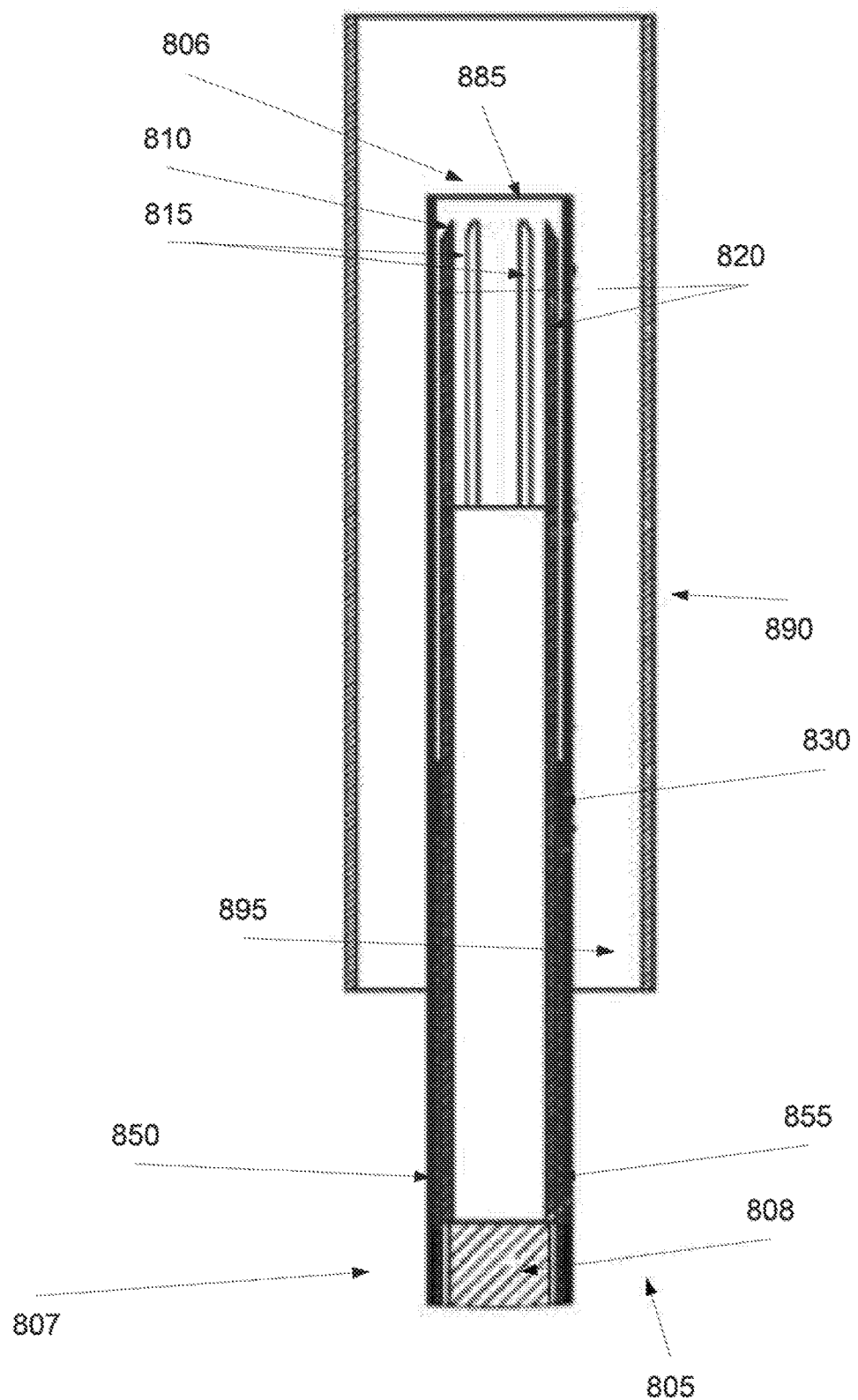
FIG. 8 is a schematic illustration of an intersection of a blood vessel occlusion device in delivery state having a first and second expandable annular elements, a plurality of anchoring teeth and a retention element, according to some embodiments of the present invention.

Reference is now made to FIG. 8, which is a schematic illustration of an intersection of a blood vessel occlusion device 805 in delivery state having a first 815 and second 820 expandable annular elements, a plurality of anchoring teeth 810 and a retention element 830, according to some embodiments of the present invention. The blood vessel occlusion device 805 is as described in FIG. 7. The blood vessel occlusion device 805 is shown in a blood vessel represented by vessel walls 845. The first 815 and second 820 expandable annular elements are substantially aligned along a common longitudinal axis. A retention element 830 is in a deployment device 885 along with a ring pushing element 850. The blood vessel occlusion device 805 has a front side 806 and a back side 807. A retention element moving component 855 may be located behind the retention element 830. The retention element 830 may be moved by a retention element moving component 855. The retention element moving component 855 may move forward towards the front side 806 to place the retention element 830 in its destination position, for example encircling the second expandable annular element 820. Then, the retention element moving component 855 may be pulled backwards towards the rear side 807 without pulling the retention element 830 along with it. The retention element 830 may be a ring. The ring 830 may be pushed from a rear location behind the first expandable annular element 815 and/or behind the second expandable annular element 820 to retain the first 815 and/or second 820 expandable annular element. The retention may be partial, keeping the expandable annular element(s) 815, 820 in a middle configuration between a delivery state and a deployed state. The retention element 830 may encircle the second expandable annular element 820. The retention element 830 may limit the width of the second expandable annular element 820. The blood clot cage may be essentially in front of the second annular element 820.

Figure 9:
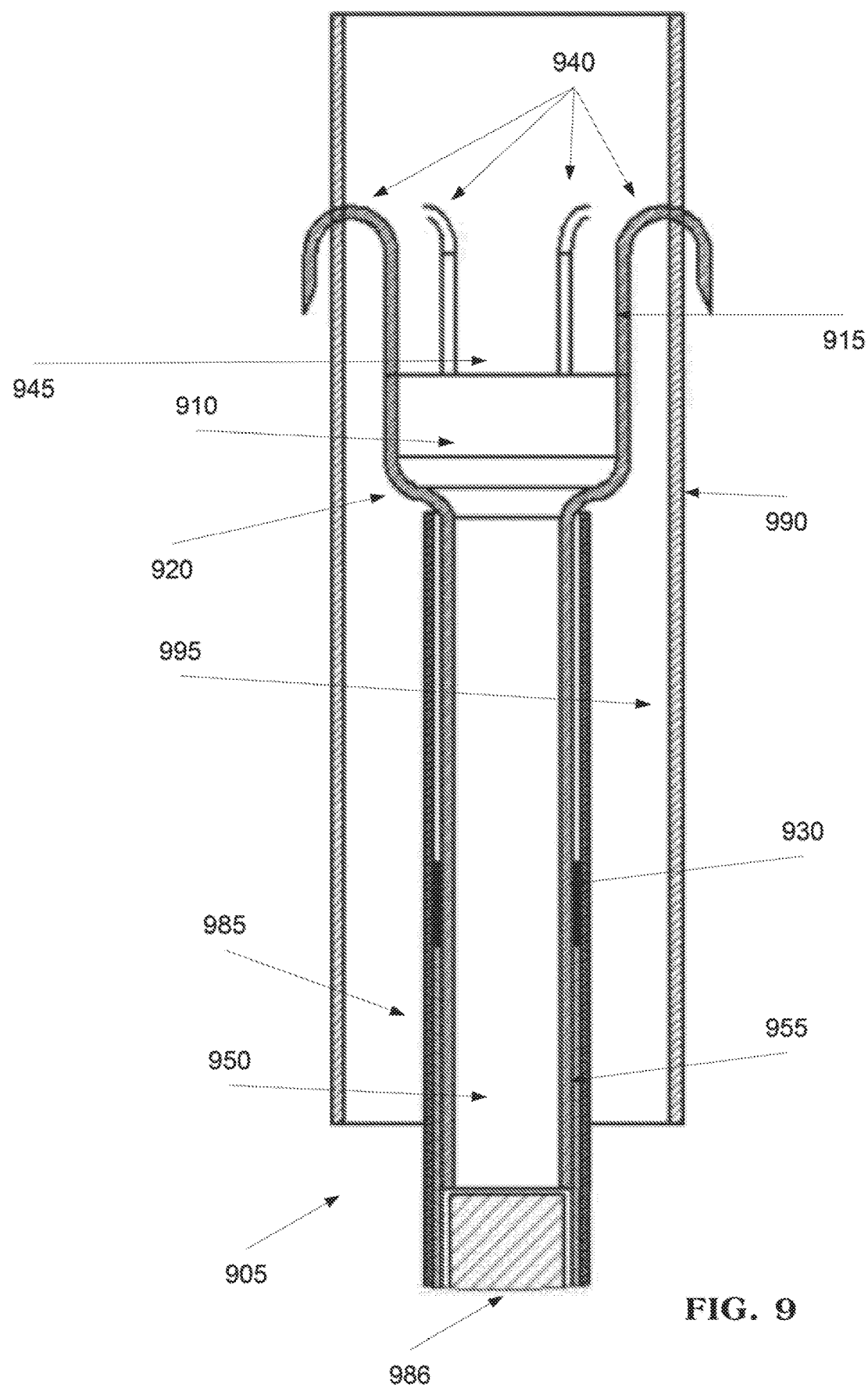
FIG. 9 is a schematic illustration of an intersection of a blood vessel occlusion device having a first expandable annular element is a deployed state and a second expandable annular element is a delivery state, according to some embodiments of the present invention.

Reference is now made to FIG. 9, which is a schematic illustration of an intersection of a blood vessel occlusion device 905 having a first expandable annular element 915 is a deployed state and as second expandable annular element 920 is a delivery state, according to some embodiments of the present invention. The blood vessel occlusion device 905 is as described in FIGS. 7 and 8.

Figure 10:
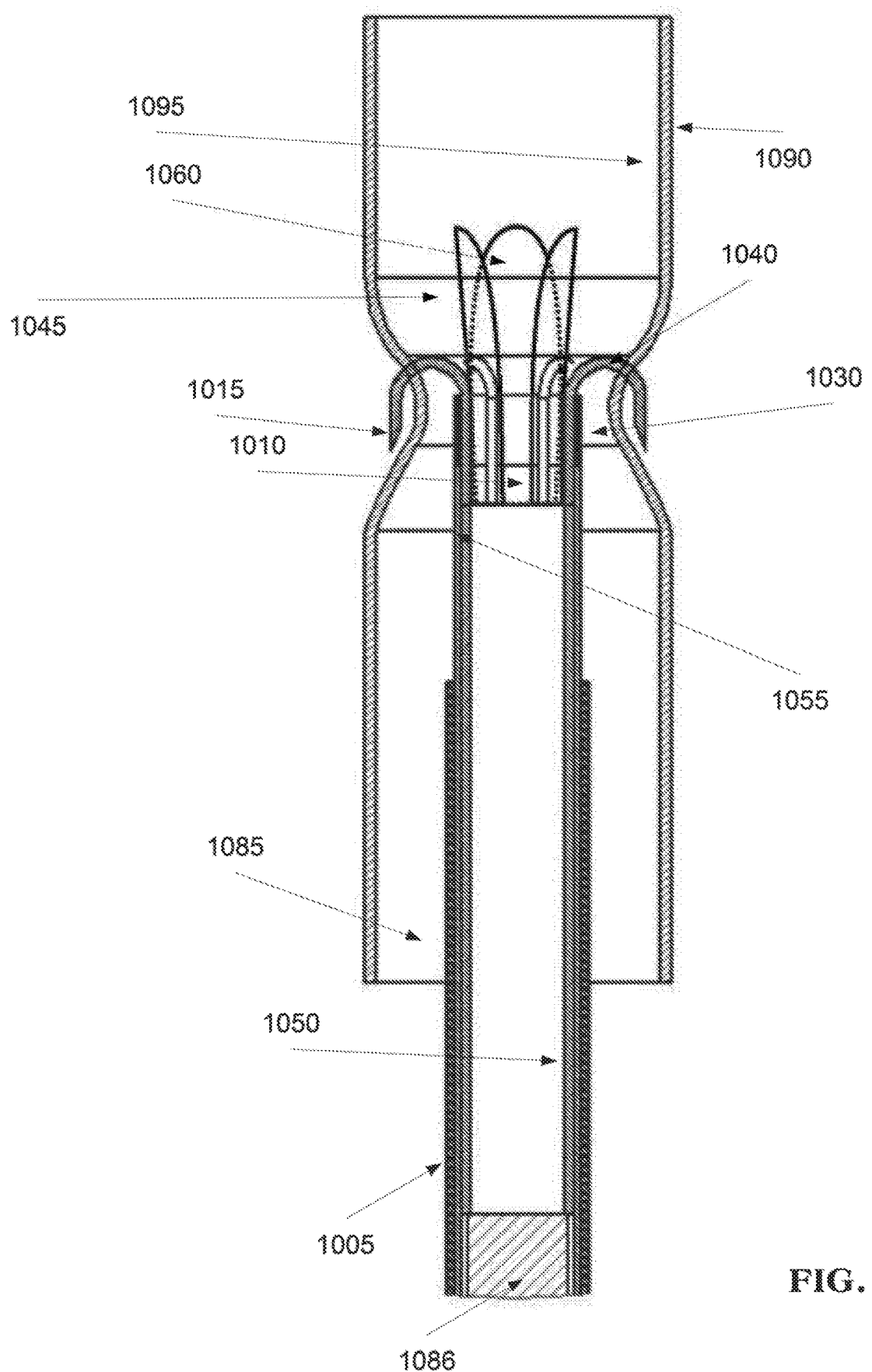
FIG. 10 is a schematic illustration of an intersection of a blood vessel occlusion device grasping blood vessel walls with a plurality of retained anchoring teeth, according to some embodiments of the present invention.

Reference is now made to FIG. 10, which is a schematic illustration of an intersection of a blood vessel occlusion device 1005 grasping blood vessel walls 1045 with a plurality of retained anchoring teeth 1010, according to some embodiments of the present invention. The blood vessel occlusion device 1005 is as described in FIG. 9, with the retention element 1030 constricting the first expandable element 1015. The vessel walls 1045 may move toward one another and/or occlusion the blood vessel. A blood clot cage 1060 is mounted on first expandable element 1015. Optionally, the blood clot cage 1060 catches blood clots which may form during occlusion process.

Figure 11:
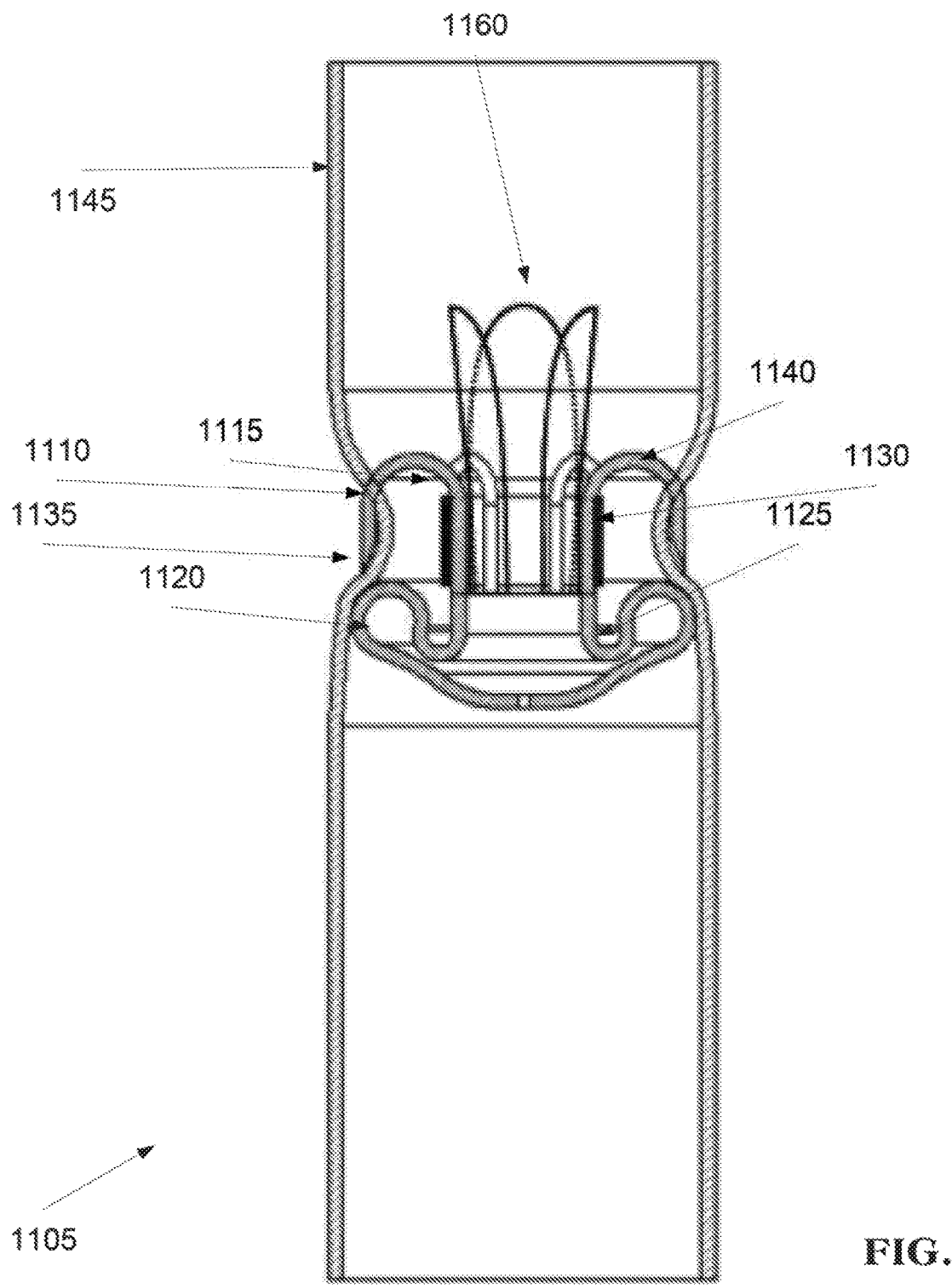
FIG. 11 is a schematic illustration of an intersection of a blood vessel occlusion device having a first and second expandable annular elements in a deployed state within a blood vessel, according to some embodiments of the present invention.

Reference is now made to FIG. 11, which is a schematic illustration of an intersection of a blood vessel occlusion device 1105 having a first 1115 and second 1120 expandable annular elements in a deployed state within a blood vessel, according to some embodiments of the present invention. The blood vessel occlusion device 1105 is as described in FIG. 10 with the second expandable element 1120 in a deployed state and the deployment device 1185 removed. The retention element 1130 essentially encircles the first expandable annular element 1115. There may be a groove 1125 between the first expandable annular element 1115 and the second expandable annular element 120. Optionally, the groove 1125 supports said retention element, preventing the retention element from sliding off the second expandable annular element 120. Optionally, the blood vessel wall 1145 is grasped between the anchoring teeth 1110 and the second expandable annular element 1120.

Figure 12:
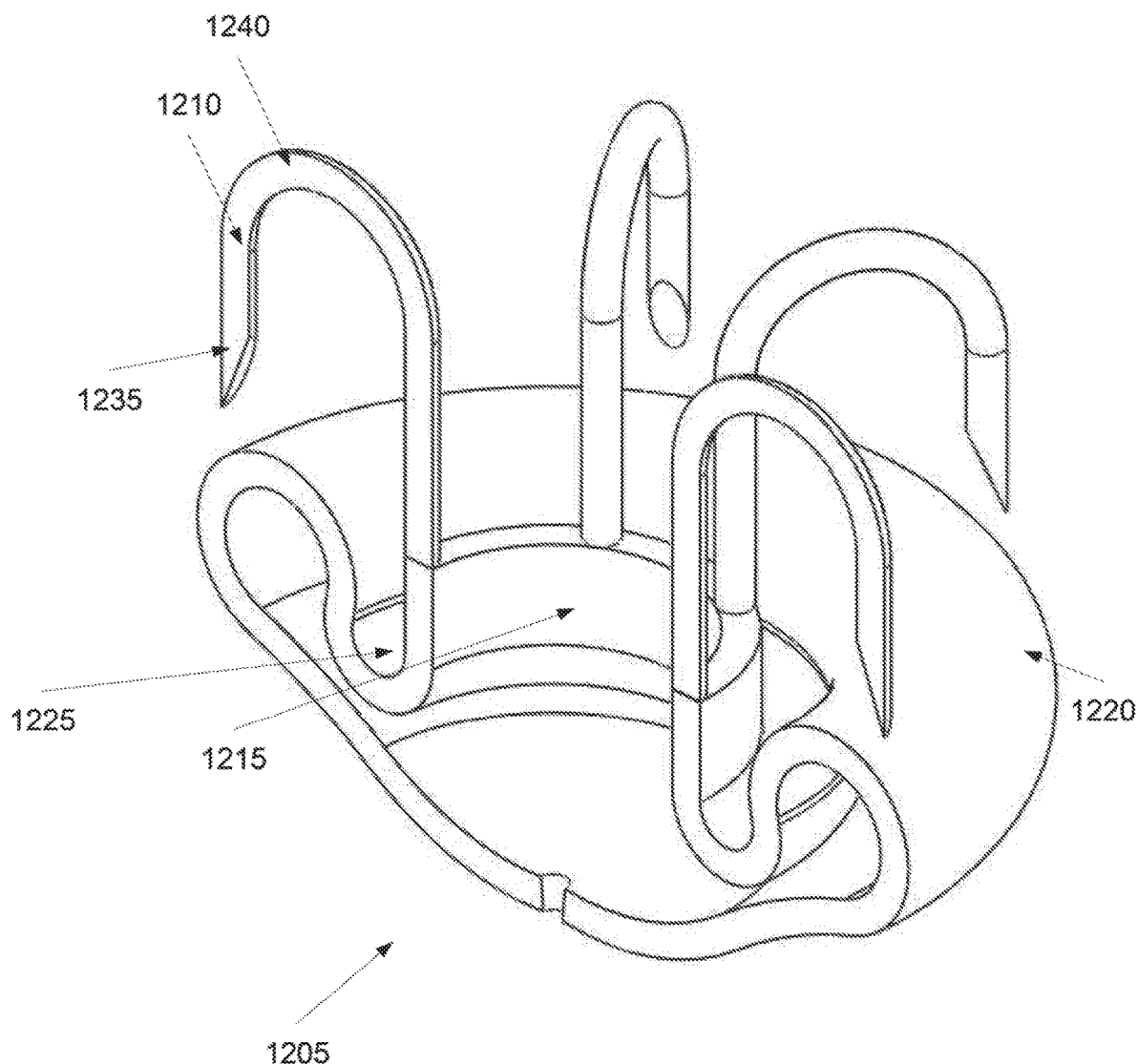
FIG. 12 is a 3D schematic illustration of an intersection of a blood vessel occlusion device having a first and second expandable annular elements in deployed state and a plurality of anchoring teeth, according to some embodiments of the present invention.

Reference is now made to FIG. 12, which illustrates a 3D schematic illustration of an intersection of a blood vessel occlusion device 1205 having first 1215 and second 1220 expandable annular elements in deployed state and a plurality of anchoring teeth 1210, according to some embodiments of the present invention. The blood vessel occlusion device 1205 is as described in FIG. 7.

Figure 13:
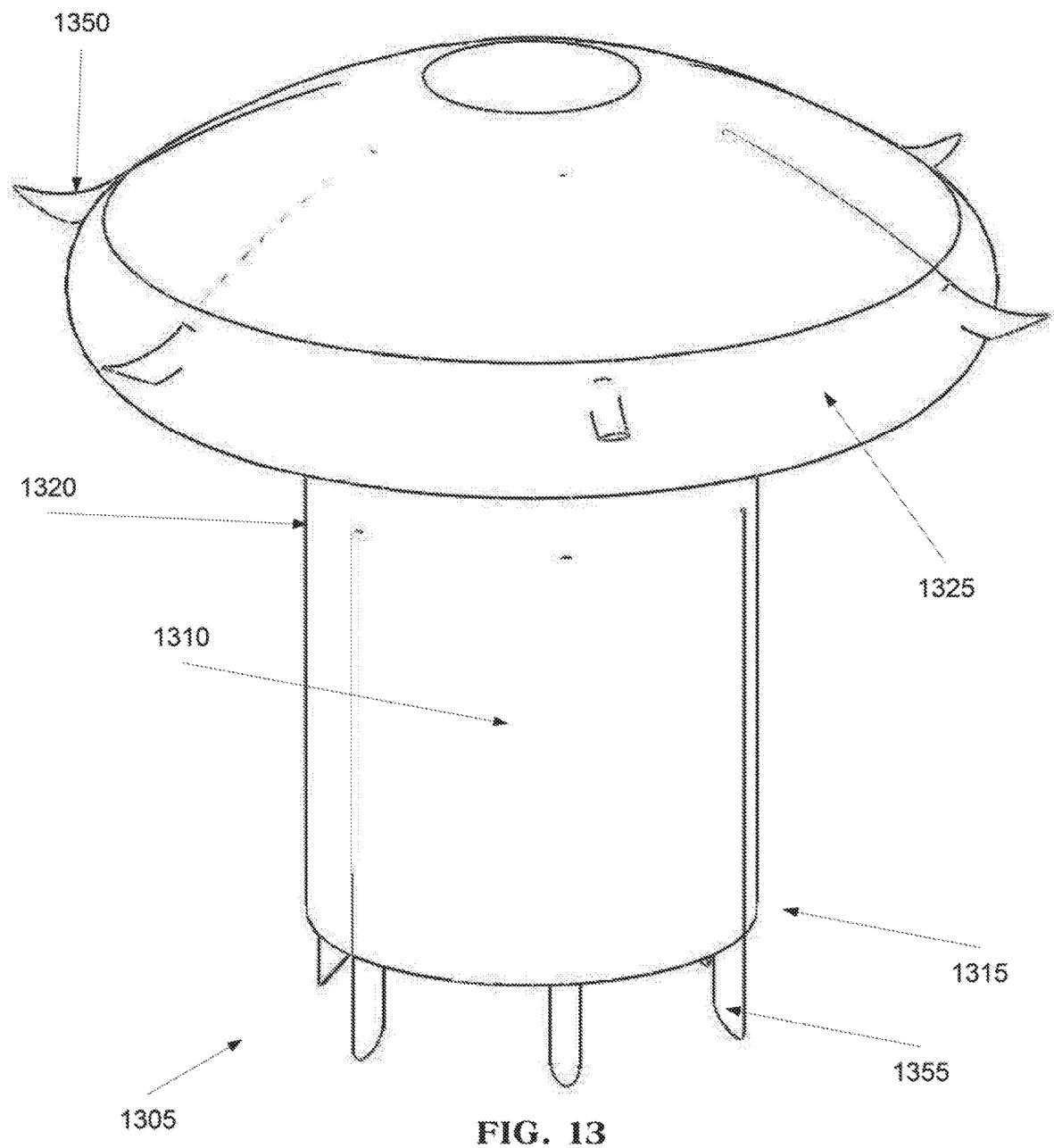
FIG. 13 is a 3D schematic view of a blood vessel occlusion device having an expandable tubular frame, according to some embodiments of the present invention.

Reference is now made to FIG. 13, which illustrates the 3D schematic view of a blood vessel occlusion device 1305 having an expandable tubular frame 1310, according to some embodiments of the present invention. The tubular frame 1310 has an upper end 1320 and a lower end 1315. An expandable ring 1325 encircles the upper end 1320. The expandable ring 1325 is essentially perpendicular to the expandable tubular frame 1310. The expandable ring 1325 perpendicular position may achieved by banding towards exterior side 1365 then towards interior side 1360 and/or towards interior side 1360 then towards exterior side 1365. The blood vessel occlusion device 1305 may be deployed using a deployment device, for example a catheter and/or a syringe. The deployment device may be made of a flexible material capable of curving along the natural curves of a target blood vessel. The deployment device is sized and shaped to fit into and/or to be pushed along a target blood vessel. The expandable ring 1325 and the expandable tubular frame 1310 are sized and shaped to fit for pushing into a target blood vessel. The expandable ring 1325 essentially occupies a target blood vessel lumen when in a deployed state. The expandable ring 1325 may be a tube shape when in a delivery state and/or take essentially the shape of the deployment device. The expandable ring 1325 and/or the expandable tubular frame 1310 may have a plurality of anchoring teeth 1350, 1355. The anchoring teeth 1350, 1355 may be capable of grasping a blood vessel wall. The blood vessel occlusion device 1305 may also have a retention element.

Figure 14:
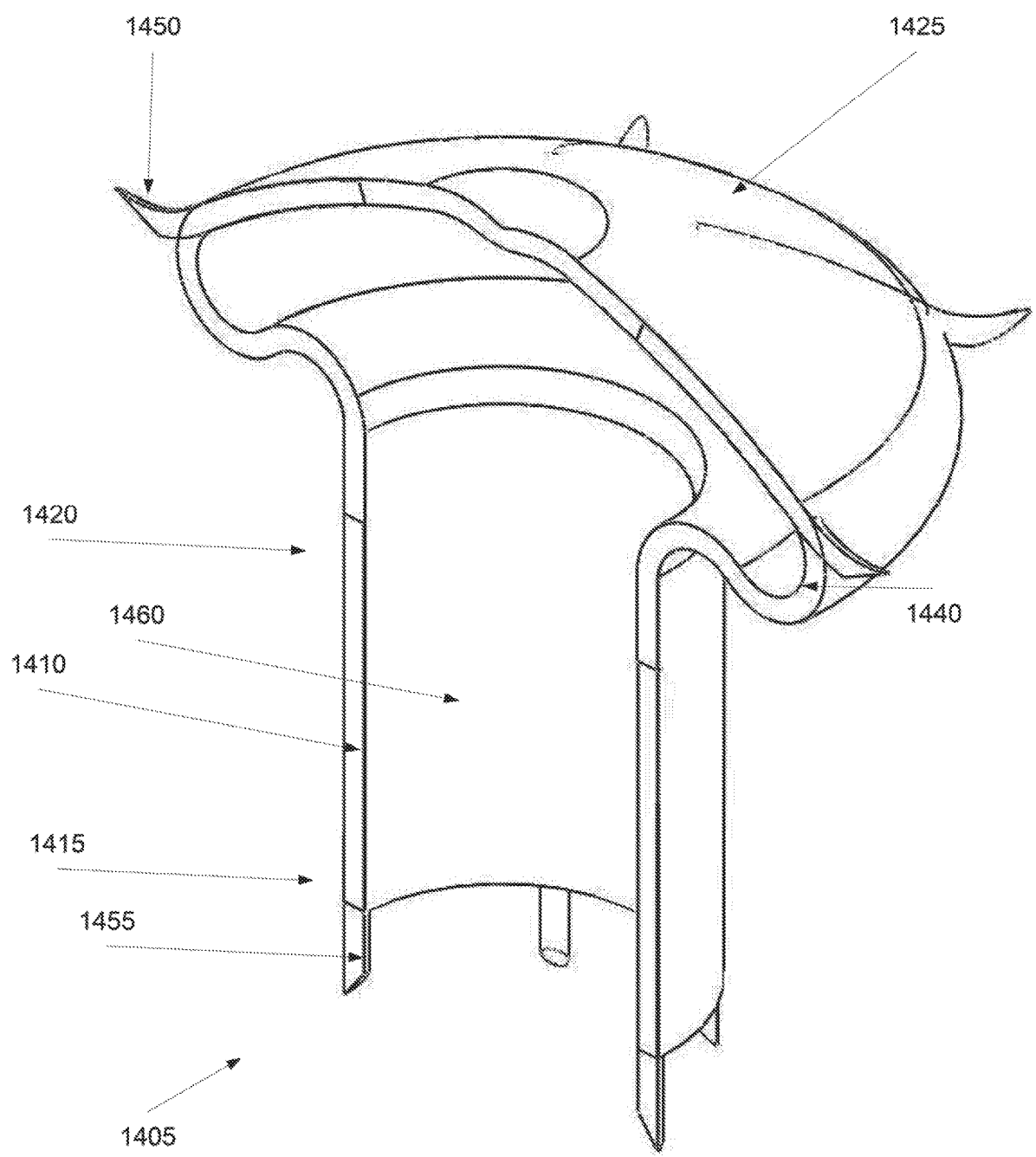
FIG. 14 is a 3D schematic crosscut view of a blood vessel occlusion device, according to some embodiments of the present invention.

Reference is now made to FIG. 14, which is a 3D schematic crosscut view of a blood vessel occlusion device 1405, according to some embodiments of the present invention. The blood vessel occlusion device 1405 is as described in FIG. 13.

Figure 15:
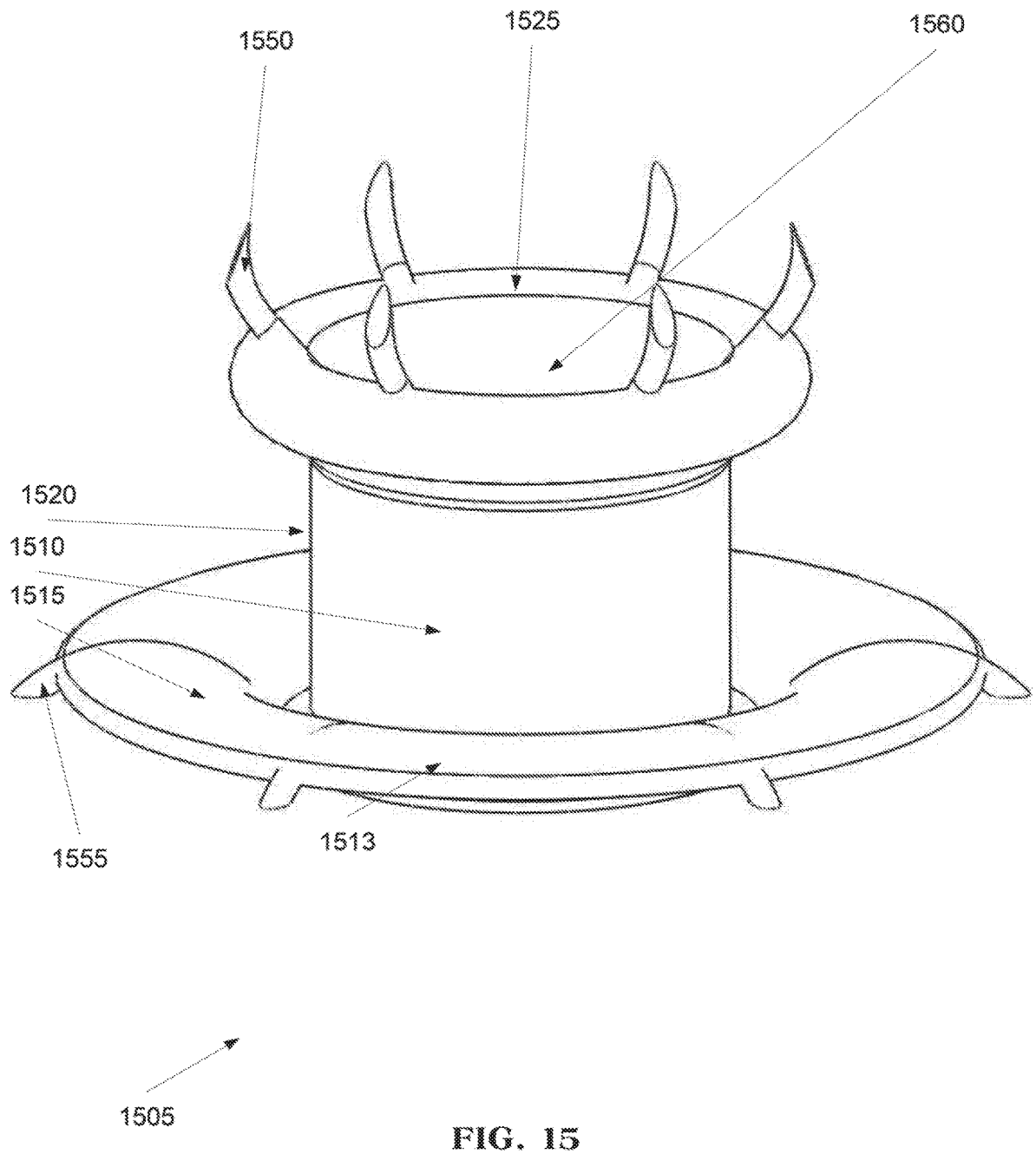
FIG. 15 is a 3D schematic view of a blood vessel occlusion device with the upper end of an expandable tubular frame inside the expandable tubular frame, according to some embodiments of the present invention.

Reference is now made to FIG. 15, which is a 3D schematic view of a blood vessel occlusion device 1505 with the upper end 1520 of an expandable tubular frame 1510 inside the expandable tubular frame 1510, according to some embodiments of the present invention. The blood vessel occlusion device 1505 is as described in FIG. 13. The upper end 1520 is pulled into the expandable tubular frame 1510. The upper anchoring element 1550 may change its location and angle with respect to the blood vessel wall and/or the expandable ring 1525. The orientation change of the upper anchoring element 1550 may enhance the anchoring of the upper anchoring element 1550 into a target blood vessel wall. Optionally, the upper end 1520 is pulled into the expandable tubular frame 1510 using a pulling rode and/or a pulling wire.

Figure 16:
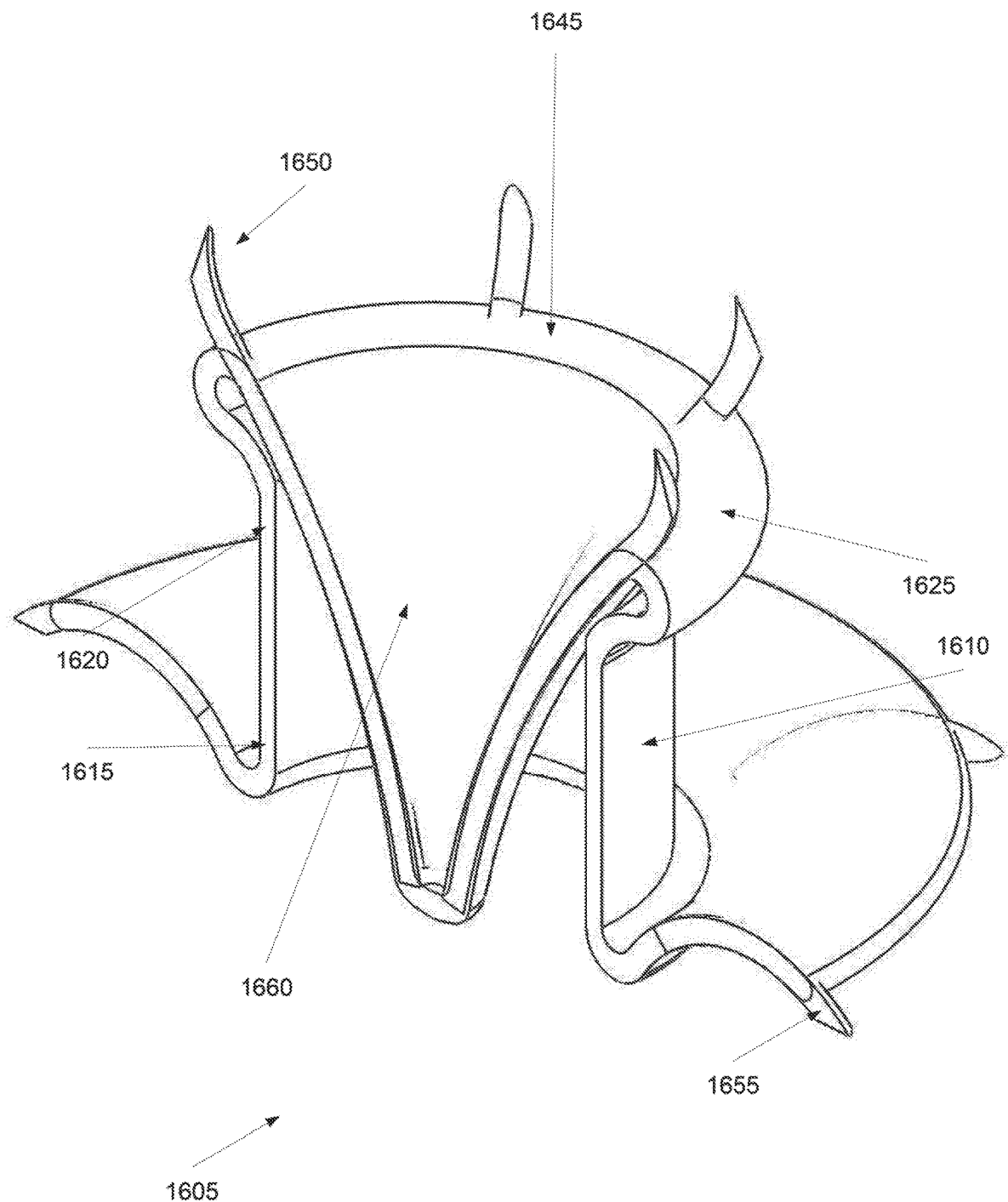
FIG. 16 is a schematic illustration of an intersection of a blood vessel occlusion device having an expandable tubular frame, according to some embodiments of the present invention.

Reference is now made to FIG. 16, which is a schematic illustration of illustrates an intersection of a blood vessel occlusion device 1605 having an expandable tubular frame 1610, according to some embodiments of the present invention. The blood vessel occlusion device 1605 is as described in FIG. 13.

Figure 17:
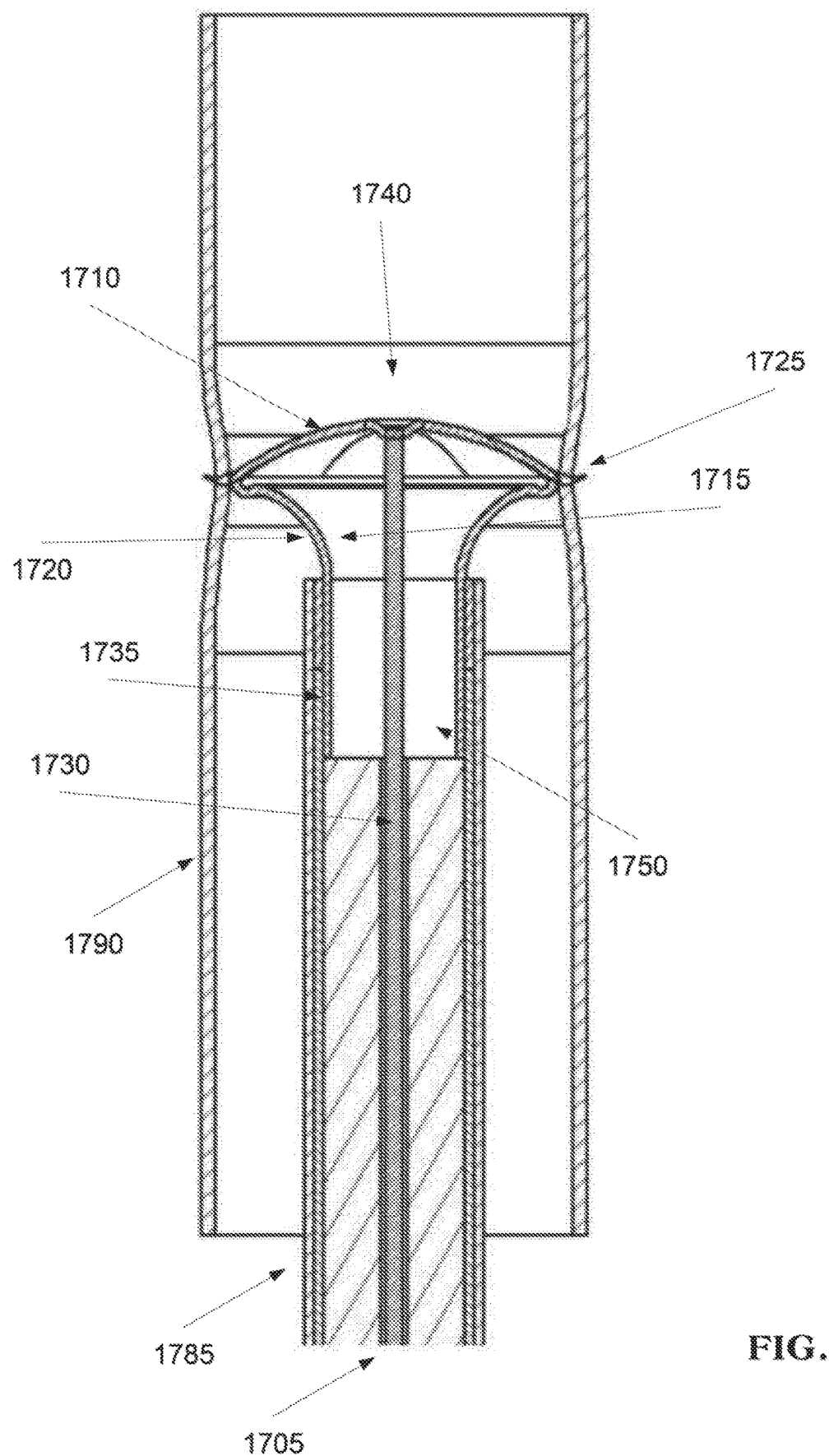
FIG. 17 is a schematic illustration of a blood vessel occlusion device in an unturned mode, having an expandable sleeve and a pulling wire protruding into a blood vessel wall, according to some embodiments of the present invention.

Reference is now made to FIG. 17, which is a schematic illustration of a blood vessel occlusion device 1705 in an unturned mode, having an expandable sleeve and a pulling wire protruding into a blood vessel wall, according to some embodiments of the present invention. The blood vessel occlusion device 1705 comprises an expandable sleeve 1710. The expandable sleeve 1710 has an unturned mode and a turned mode. The outer side 1720 faces outside of the expandable sleeve 1710 when in unturned mode. The outer side 1720 faces inside of the expandable sleeve 1710 when in turned mode. Optionally, the expandable sleeve 1710 is thermally treated. A plurality of anchoring teeth 1725 are mounted on the outer side 1720 of the expandable sleeve 1710. The plurality of anchoring teeth 1725 is capable of grasping a vein's wall 1790. A pulling wire 1730 attached to the expandable sleeve 1710. Optionally, the pulling wire 1730 is attached to the inner side 1715 of the expandable sleeve 1710. Optionally, the pulling wire 1730 is attached to the tip of the outer side 1720 of the expandable sleeve 1710. Upon pulling, the pulling wire 1730 flips the expandable sleeve 1710 inside out, thereby transforming the expandable sleeve 1710 from an unturned mode. Flipping itself may reduce the expandable sleeve perimeter by about 10-40%. A retention element 1735 is positioned to wrap around the expandable sleeve 1710. The retention element restricts the dimensions of the expandable sleeve 1710.

Figure 18:
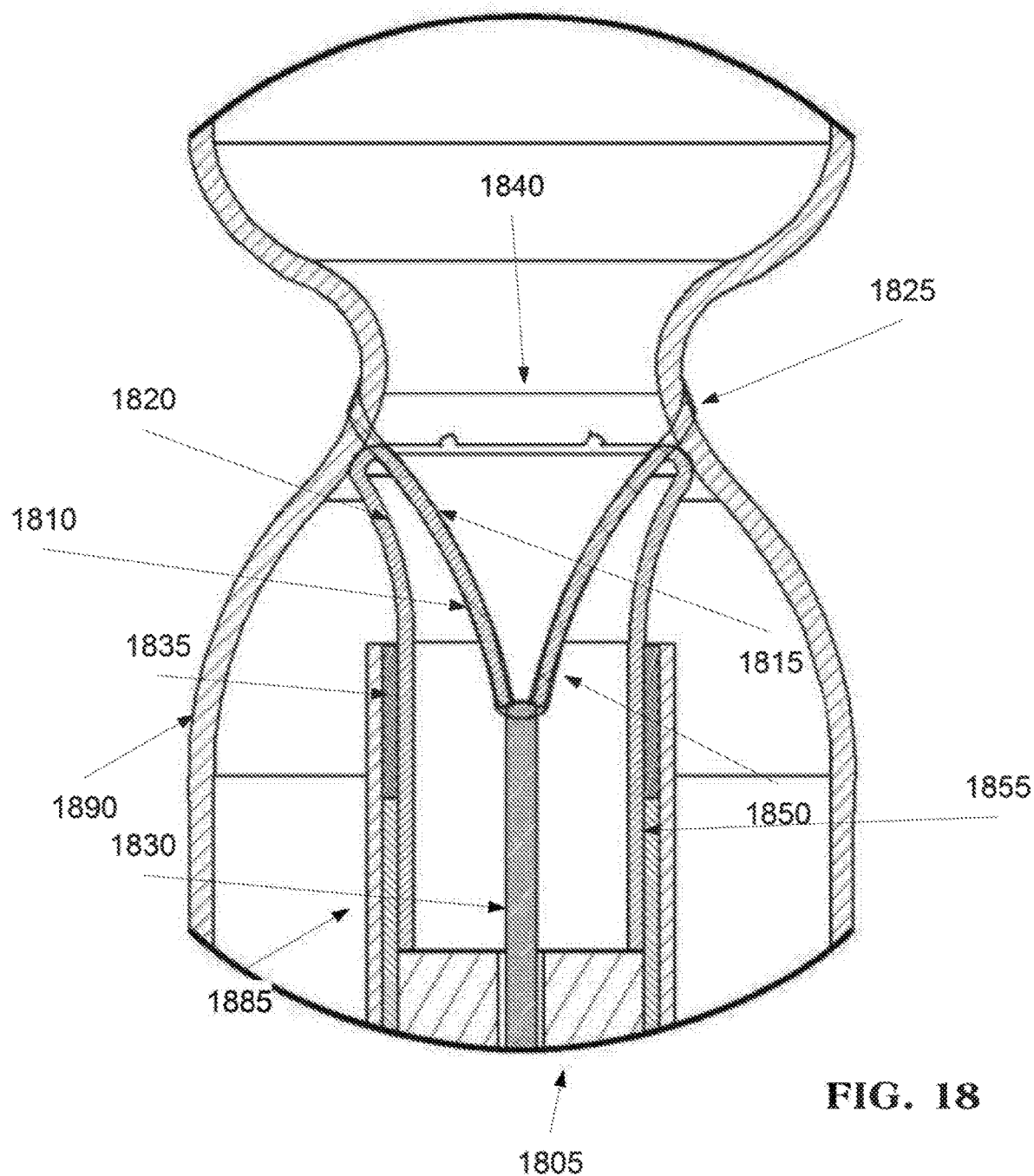
FIG. 18 is a schematic illustration of a blood vessel occlusion device having an expandable sleeve pulled back by a, according to some embodiments of the present invention.

Reference is now made to FIG. 18 which illustrates a schematic a blood vessel occlusion device 1805 having an expandable sleeve 1810 pulled back by a pulling wire 1830, according to some embodiments of the present invention. The blood vessel occlusion device 1805 is a turned mode. Optionally, a deployment device 1885 limits the expansion of said expandable sleeve 1810 and is capable of delivering the blood vessel occlusion device 1805 to a target blood vessel 1890. Optionally, the deployment device 1885 delivers the blood vessel occlusion device 1805 up to about 1 meter (m) into a target blood vessel, enabling to push the device 1805 along the vessel natural curvatures. The blood vessel occlusion device 1805 is released from the deployment device 1885. The plurality of anchoring teeth 1825 grasps a vein's wall 1890. The pulling wire 1830 is pulled towards the rear side 1850 transforming the expandable sleeve 1810 from an unturned mode into a turned mode. Optionally, the target vein, represented here by a vein's wall 1890, is occluded upon this transformation. The retention element 1835 may be positioned at the expandable sleeve's 1810 rear side 1850. The retention element 1835 may restrict the expandable sleeve 1810 in the turned mode.

Figure 19:
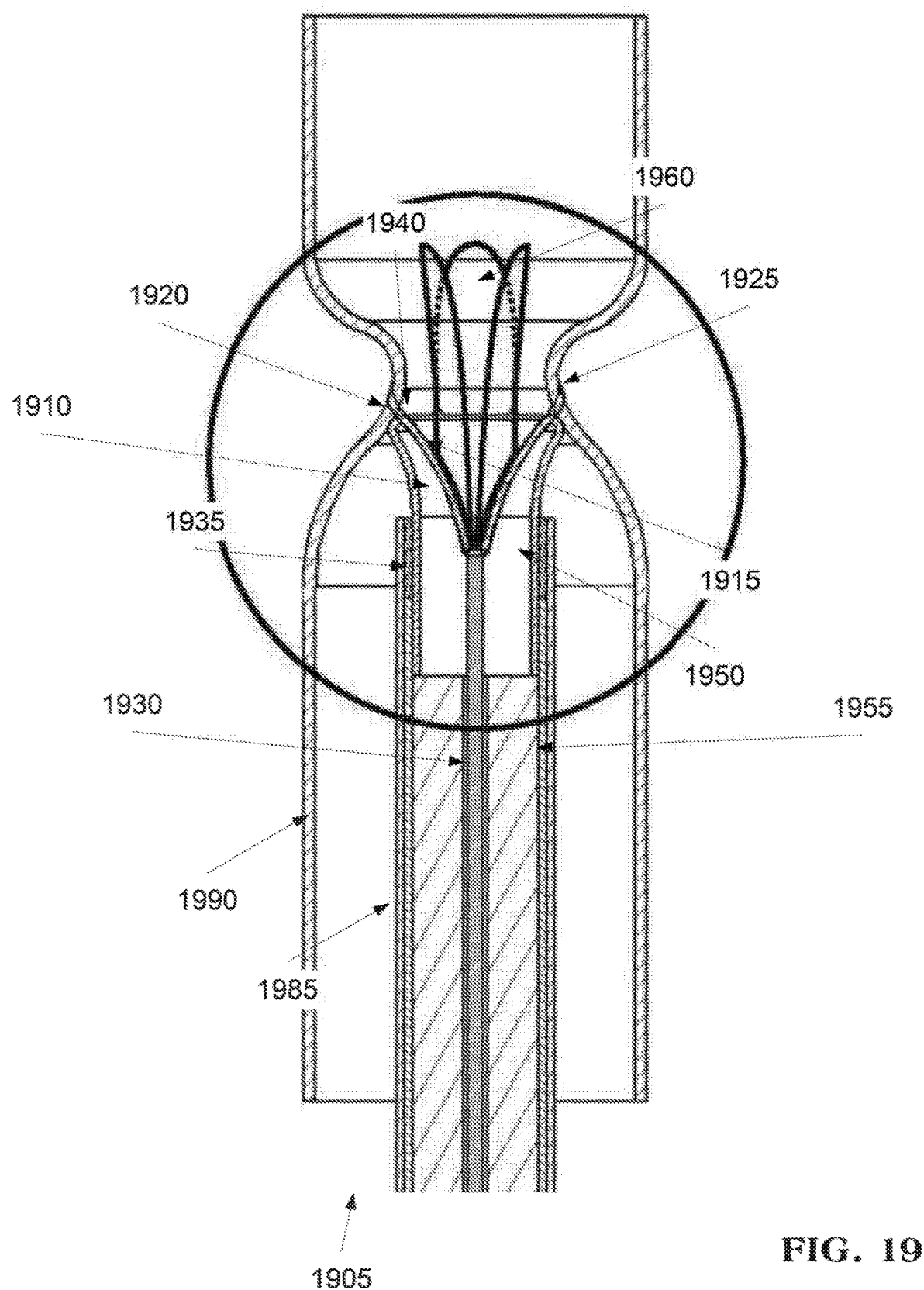
FIG. 19 is a schematic illustration of a blood vessel occlusion device having an expandable sleeve and a pulling wire and a blood clot cage, according to some embodiments of the present invention.

Reference is now made to FIG. 19 is a schematic illustration of a blood vessel occlusion device 1905 having an expandable sleeve and a pulling wire and a blood clot cage 1960, according to some embodiments of the present invention. The blood vessel occlusion device 1905 is as described in FIG. 18. Optionally, the blood clot cage 1960 is essentially in front of the front side 1940.

Figure 20:
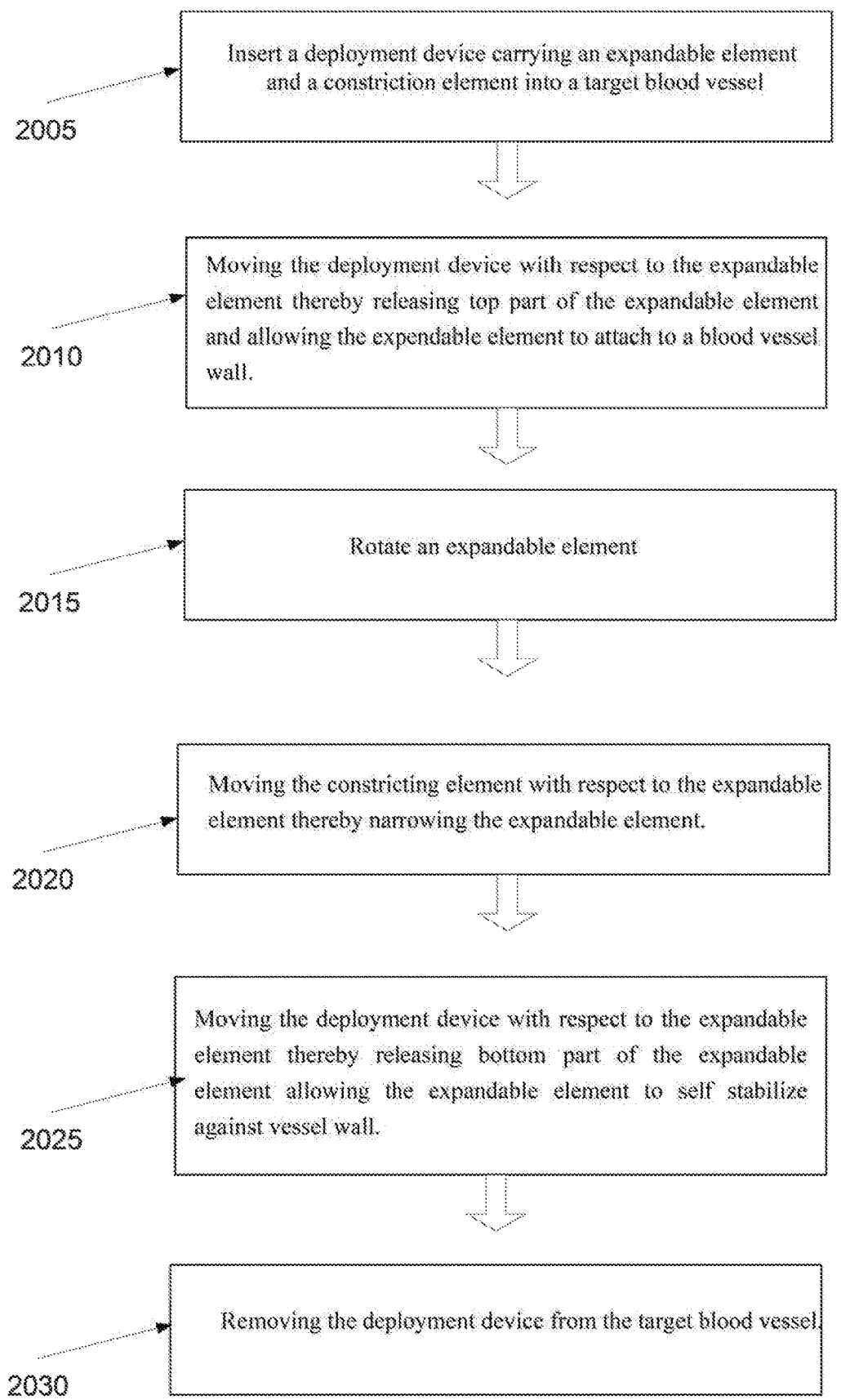
FIG. 20 is a schematic illustration of a method for occluding a blood vessel, according to some embodiments of the present invention.

Reference is now made to FIG. 20 which is a flowchart of a method for occluding a blood vessel, according to some embodiments of the present invention. First a deployment device carrying an expandable element and a constriction element is inserted into a target blood vessel 2005. The deployment device may curve along the blood vessel, for instance along about 1 meter (m) or even more, fitting in shape to the natural curves of the target blood vessel. Then, the deployment device is moved with respect to the expandable element 2010. The top part of the expandable element is released, allowing the expandable element to attach to a blood vessel wall. Optionally, the expandable element is then rotated 2015. Next, the constricting element is moved with respect to the expandable element thereby narrowing the expandable element 2020 and the deployment device is navigated with respect to the expandable element thereby releasing bottom part of the expandable element allowing the expandable element to stabilize against vessel wall 2025. Navigation may be achieved by holding the deployment device static and moving the expandable element. Optionally, navigation is achieved by holding the expandable element static and moving the deployment device and/or by dual movement of both the deployment device and the expandable element with respect to one another in different directions. The stabilization of the expandable element against a vessel wall may be self stabilization, which is unsupported by additional elements. Optionally, the self stabilization is achieved by the size and shape of the expandable element which fit the dimensions of a target blood vessel and/or by applying pressure on the walls of said blood vessel. Optionally, a deployment device is removed 2030. Optionally, an occluding agent is released after one of the steps 2005-2030.

Figure 21:
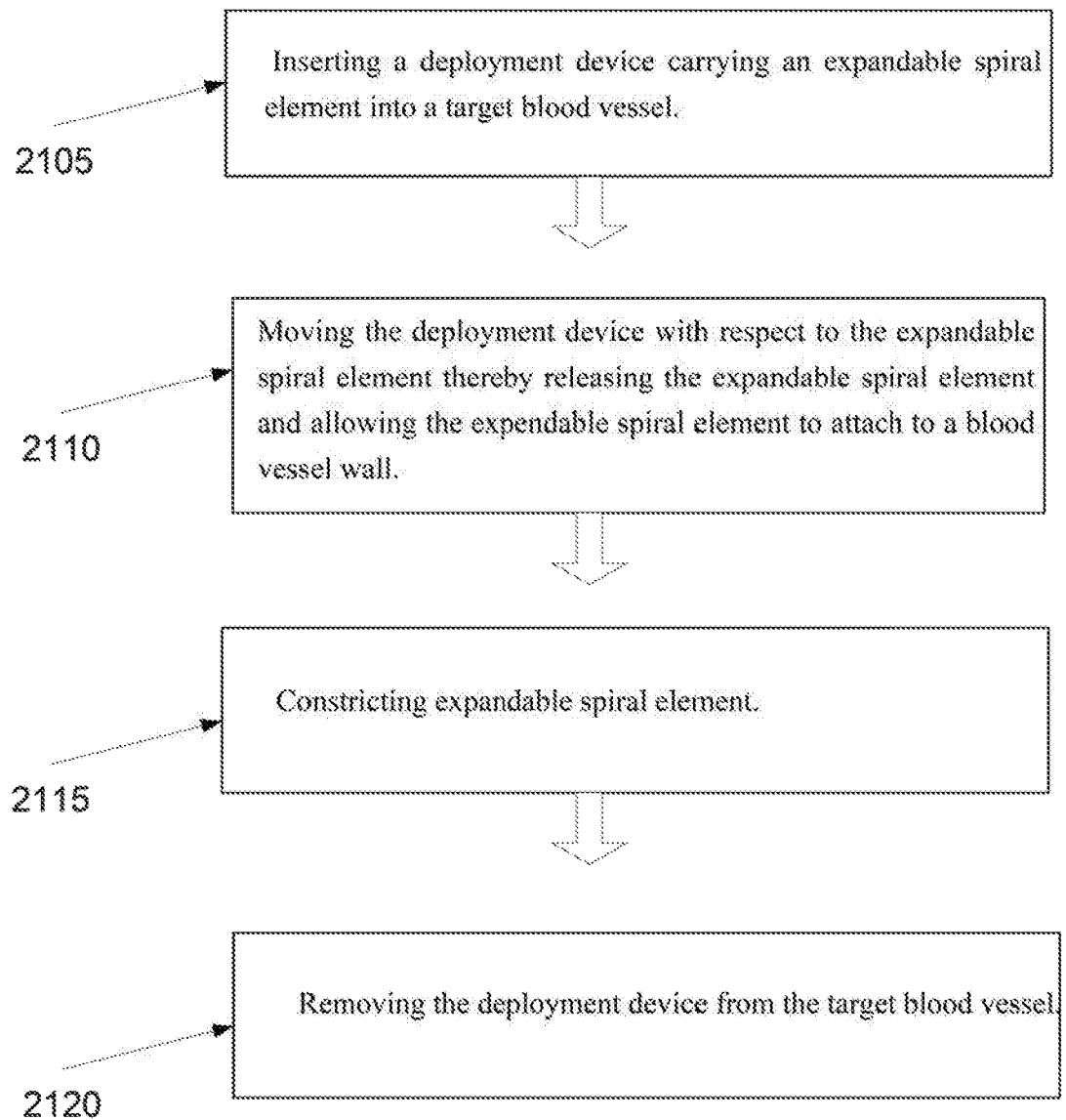
FIG. 21 is a schematic illustration of another method for occluding a blood vessel, according to some embodiments of the present invention.

Reference is now made to FIG. 21 which is a flowchart of a method for occluding a blood vessel, according to some embodiments of the present invention. First, a deployment device carrying an expandable spiral element is inserted into a target blood vessel 2105 as described in FIG. 20 step 2005. Next, the deployment device is moved with respect to the expandable spiral element thereby releasing the expandable spiral element and allowing said expandable spiral element to attach to a blood vessel wall 2110. Then, the expandable spiral element is constricted 2115. Optionally, the deployment device is then removed 2120. Optionally, an occluding agent is released after one of the steps 2105-2120.

Figure 22:
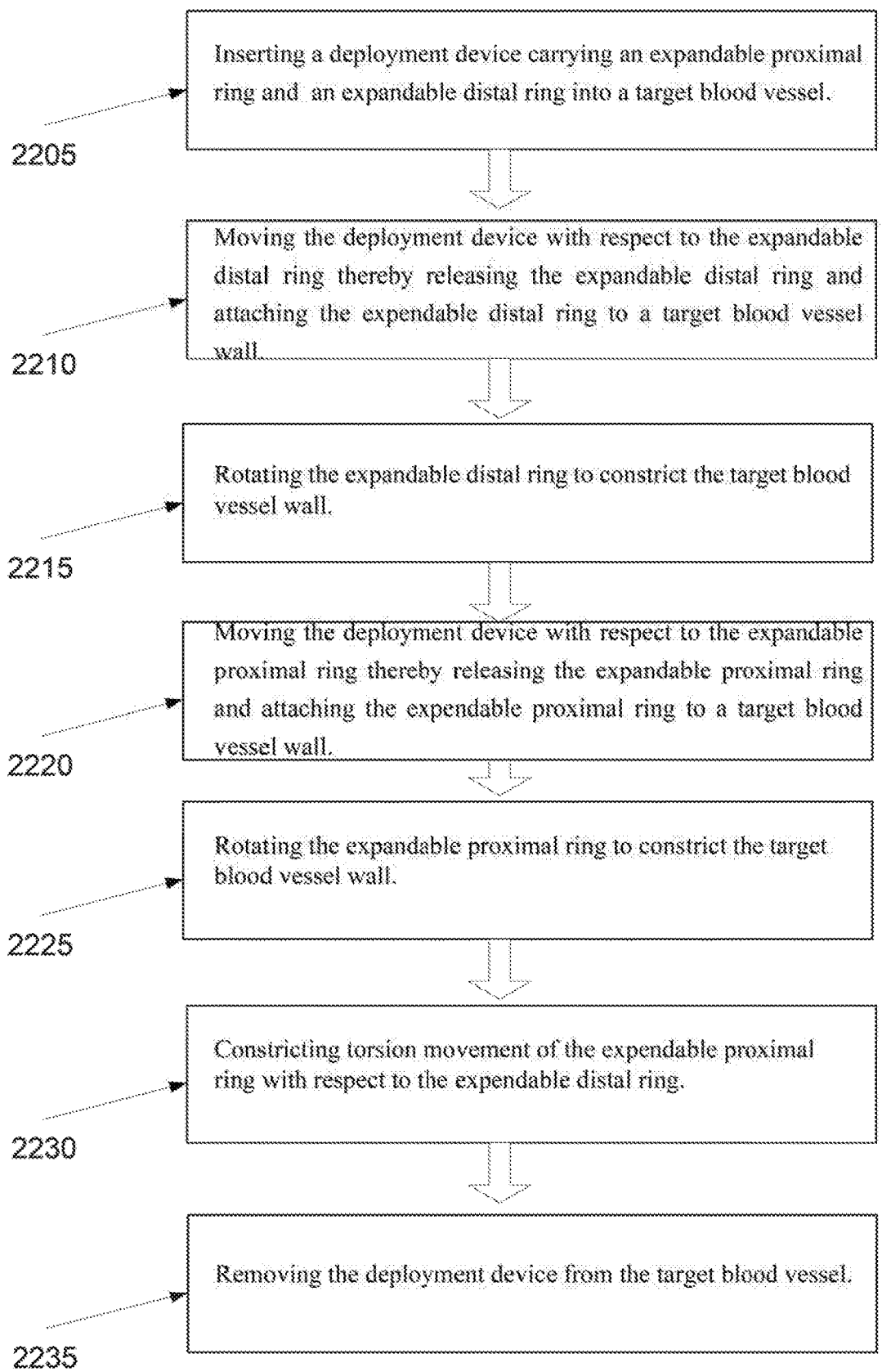
FIG. 22 is a schematic illustration of another method for occluding a blood vessel, according to some embodiments of the present invention.

Reference is now made to FIG. 22 which is a flowchart of a method for occluding a blood vessel, according to some embodiments of the present invention. First, a deployment device carrying an expandable proximal ring and an expandable distal ring is inserted into a target blood vessel 2205 as described in FIG. 20 step 2005. Next, the deployment device is moved with respect to the expandable distal ring thereby releasing the expandable distal ring and attaching the expandable distal ring to a target blood vessel wall 2210. Then, the expandable distal ring is rotated to constrict the target blood vessel wall 2215. The rotation of the expandable distal ring may be in counter direction with respect to rotation of the expandable proximal ring. Then, the deployment device is moved with respect to the expandable proximal ring thereby releasing the expandable proximal ring and attaching the expandable proximal ring to a target blood vessel wall 2220. Then, the expandable proximal ring is rotated to constrict the target blood vessel wall 2225. Then, the expandable proximal ring's torsion movement is constricted with respect to said expandable distal ring 2230. Optionally, the deployment device is then removed from the target blood vessel 2235. Optionally, an occluding agent is released after one of the steps 2205-2235.

Figure 23:
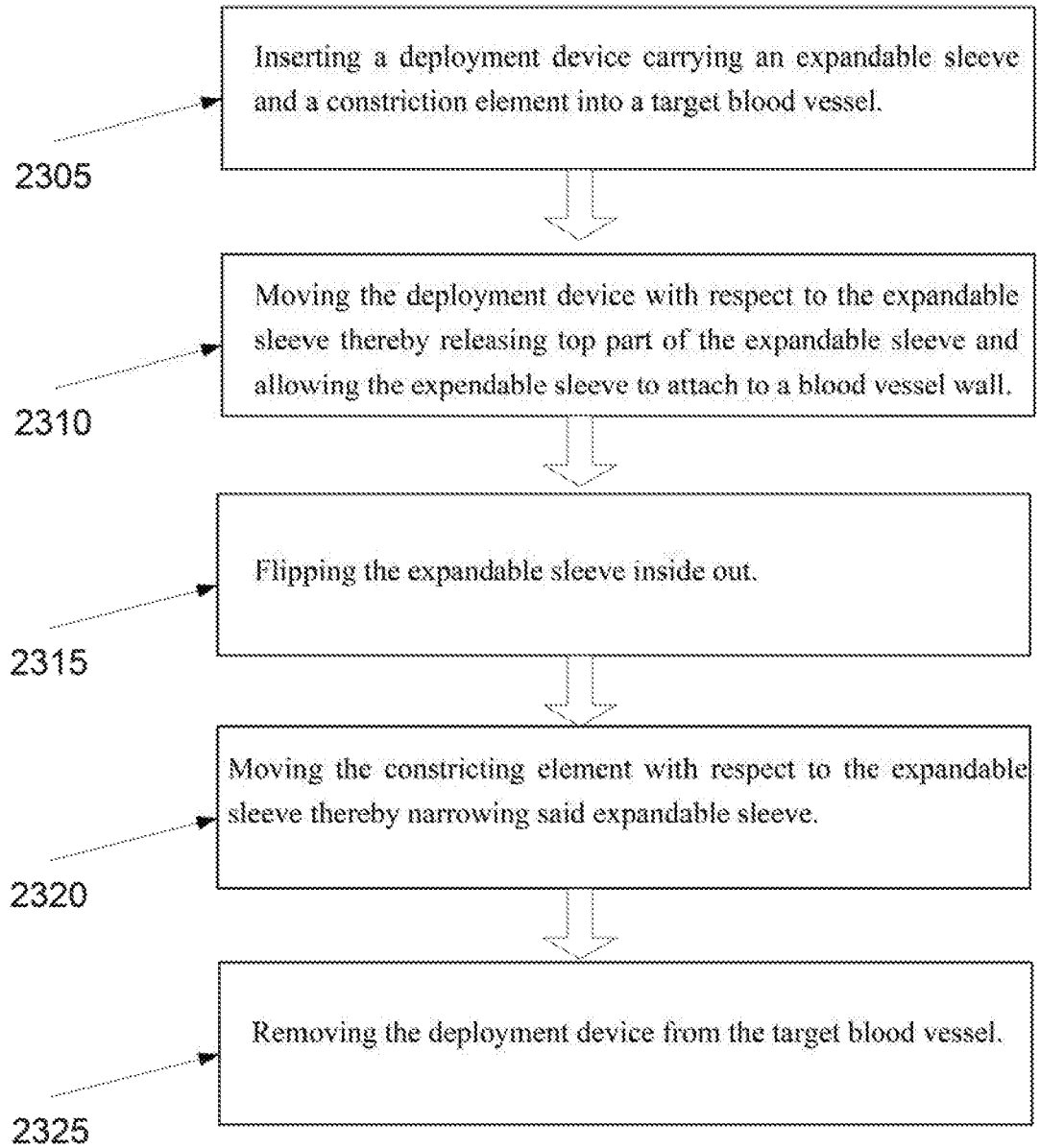
FIG. 23 is a schematic illustration of another method for occluding a blood vessel, according to some embodiments of the present invention.

Reference is now made to FIG. 23 which is a flowchart of a method for occluding a blood vessel, according to some embodiments of the present invention. First, a deployment device carrying an expandable sleeve and a constriction element is inserted into a target blood vessel 2305. Next, the deployment device is moved with respect to the expandable sleeve thereby releasing top part of the expandable sleeve and allowing the expandable sleeve to attach to a blood vessel wall 2310. Then, the expandable sleeve is flipped inside out 2315. Then, the constricting element is moved with respect to the expandable sleeve thereby narrowing said expandable sleeve 2320. Optionally, the deployment device is then removed from the target blood vessel 2325. Optionally, an occluding agent is released after one of the steps 2305-2325.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

It is expected that during the life of a patent maturing from this application many relevant shape memory alloys and/or deployment devices will be developed and the scope of the term shape memory alloys and/or deployment devices is intended to include all such new technologies a priori As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A blood vessel occlusion device comprising:
a plurality of legs having a deployed state wherein each of said plurality of legs is angled outwardly toward an interior vessel wall of a blood vessel, away from a common longitudinal axis and a delivery state wherein said plurality of legs are sized and shaped to curve along the interior of said blood vessel and substantially in parallel to the common longitudinal axis, each said leg having an anchoring tooth at a distal end thereof, wherein each anchoring tooth is angularly connected to its respective leg, and wherein, in the deployed state, the plurality of legs are arranged in a substantially conical orientation, and the plurality of anchoring teeth are arranged in a substantially conical orientation that radially overlaps the plurality of legs;
and an annular retention element that is movable over the plurality of legs to pull them toward each other and toward the common longitudinal axis;
wherein, when each anchoring tooth is anchored to a blood vessel wall, movement of the annular retention element over the legs pulls the legs toward the common longitudinal axis, thereby completely occluding the blood vessel.

2. The blood vessel occlusion device according to claim 1, wherein each said leg switches from said deployed state to said delivery state by a retention element.

3. The blood vessel occlusion device according to claim 1, wherein said plurality of legs is made of a shape memory alloy.

4. A blood vessel occlusion device comprising:
- a tubular deployment element;
- a retention element; and
- a plurality of legs adapted to be threaded along said tubular deployment element and having a deployed state wherein each leg of said plurality of legs is angled outwardly toward an interior vessel wall, away from a common longitudinal axis, and a delivery state wherein said plurality of legs are sized and shaped for pushing into a target blood vessel and substantially in parallel to the common longitudinal axis, said each leg having an anchoring tooth at a distal end thereof and a gripping point formed therealong, wherein each anchoring tooth is angularly connected to its respective leg, and wherein, in the deployed state, the plurality of legs are arranged in a substantially conical orientation, and the plurality of anchoring teeth are arranged in a substantially conical orientation that radially overlaps the plurality of legs;

wherein said each leg switches from said deployed state to said delivery state by moving said retention element;

said retention element is releasably supportable by said gripping point;

wherein said each leg is maintained in said delivery state when said retention element is supported by said gripping point; and wherein, when each anchoring tooth is anchored to a blood vessel wall, moving the retention element such that it is supported by said gripping point pulls the legs toward the common longitudinal axis, thereby completely occluding the blood vessel.

5. The blood vessel occlusion device according to claim 4, wherein said retention element is common to at least two gripping points of said legs.

6. The blood vessel occlusion device according to claim 4, wherein said plurality of legs comprises 6 legs.

7. The blood vessel occlusion device according to claim 4, further comprising a common base wherein said plurality of legs connect to said common base.

8. The blood vessel occlusion device according to claim 4, wherein the angle between said plurality of legs is bigger in said deployed state than in said delivery state.

9. The blood vessel occlusion device according to claim 4, wherein said gripping point is a projection and said retention element is a moveable ring moveable relative to said projections and said moveable ring can be held constantly by said projections.

10. The blood vessel occlusion device according to claim 9, wherein said blood vessel occlusion device has a front side and a back side and said vessel occlusion device further comprises a ring pushing element behind said moveable ring.

11. The blood vessel occlusion device according to claim 4, wherein said delivery state fits a deployment device.

12. The blood vessel occlusion device according to claim 4, wherein said plurality of legs is made of a shape memory alloy.

13. The blood vessel occlusion device according to claim 4, wherein, upon release of the retention element from the gripping point, the leg switches from the delivery state to the deployed state.

* * * * *